United States Patent
Nicoson et al.

(10) Patent No.: US 8,430,827 B2
(45) Date of Patent: *Apr. 30, 2013

(54) VACUUM ASSISTED BIOPSY DEVICE

(75) Inventors: Zachary R. Nicoson, Indianapolis, IN (US); Jacob Flagle, New Palistine, IN (US); Michael E. Miller, Trafalgar, IN (US); Joseph L. Mark, Indianapolis, IN (US)

(73) Assignee: Suros Surgical Sysytems, Inc., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/243,419

(22) Filed: Sep. 23, 2011

(65) Prior Publication Data

US 2012/0078133 A1 Mar. 29, 2012

Related U.S. Application Data

(63) Continuation of application No. 12/205,291, filed on Sep. 5, 2008, now Pat. No. 8,048,003, and a continuation-in-part of application No. 12/039,364, filed on Feb. 28, 2008, now Pat. No. 7,988,642, and a continuation-in-part of application No. 11/389,274, filed on Mar. 24, 2006, now Pat. No. 8,357,103, which is a continuation of application No. 10/964,959, filed on Oct. 14, 2004, now Pat. No. 7,390, 306.

(60) Provisional application No. 60/970,770, filed on Sep. 7, 2007, provisional application No. 60/892,174, filed on Feb. 28, 2007, provisional application No. 60/510,866, filed on Oct. 14, 2003.

(51) Int. Cl.
*A61B 10/0275* (2006.01)

(52) U.S. Cl.
USPC .......................................................... 600/566

(58) Field of Classification Search ........... 600/564–568
See application file for complete search history.

(56) References Cited

U.S. PATENT DOCUMENTS 2,472,116 A 6/1949 Maynes
2,660,342 A 11/1953 Ruf (Continued)

FOREIGN PATENT DOCUMENTS

DE 1160573 1/1964
DE 141 108 4/1980

(Continued)

OTHER PUBLICATIONS

U.S. Appl. No. 11/389,274, filed Mar. 24, 2006.

(Continued)

*Primary Examiner* — Sean P Dougherty
*Assistant Examiner* — Michael C Stout
(74) *Attorney, Agent, or Firm* — Vista IP Law Group LLP

(57) ABSTRACT

A biopsy device having a stylet, an outer cannula, and a vacuum chamber is disclosed. The stylet includes a lumen with an open proximal end and a tissue receiving opening near a distal end thereof. The outer cannula is slidably disposed over the stylet and has an open distal end with a cutting edge formed thereon. The vacuum chamber is in communication with the lumen of the stylet. Actuation of the outer cannula causes a vacuum to be delivered to the tissue receiving opening through the lumen of the stylet before the outer cannula advances distally.

9 Claims, 16 Drawing Sheets

U.S. PATENT DOCUMENTS

| | | | |
|---|---|---|---|
| 2,735,427 A | 2/1956 | Sullivan | |
| 2,863,452 A | 12/1958 | Ogle, Sr. | |
| 2,892,457 A | 6/1959 | Sturtz | |
| 3,401,684 A | 9/1968 | Dremann | |
| 3,456,806 A | 7/1969 | Borston | |
| 3,477,423 A | 11/1969 | Griffith | |
| 3,517,688 A | 6/1970 | Scholle | |
| 3,561,429 A | 2/1971 | Jewett et al. | |
| 3,815,604 A | 6/1974 | O'Malley et al. | |
| 3,819,091 A | 6/1974 | Hollender | |
| 3,844,272 A | 10/1974 | Banko | |
| 3,889,657 A | 6/1975 | Baumgarten | |
| 3,905,365 A | 9/1975 | Colombo | |
| 3,937,222 A | 2/1976 | Banko | |
| 3,938,505 A | 2/1976 | Jamshidi | |
| 3,945,375 A | 3/1976 | Banko | |
| 3,994,297 A | 11/1976 | Kopf | |
| 4,007,742 A | 2/1977 | Banko | |
| D243,559 S | 3/1977 | Hoyle et al. | |
| 4,019,514 A | 4/1977 | Banko | |
| 4,101,756 A | 7/1978 | Yamano | |
| 4,117,843 A | 10/1978 | Banko | |
| 4,159,773 A | 7/1979 | Losenno | |
| 4,167,943 A | 9/1979 | Banko | |
| 4,167,944 A | 9/1979 | Banko | |
| 4,210,146 A | 7/1980 | Banko | |
| 4,257,425 A | 3/1981 | Ryan | |
| 4,301,802 A | 11/1981 | Poler | |
| 4,308,878 A | 1/1982 | Silva | |
| 4,316,465 A | 2/1982 | Dotson, Jr. | |
| 4,354,093 A | 10/1982 | Zago | |
| 4,368,734 A | 1/1983 | Banko | |
| 4,461,305 A | 7/1984 | Cibley | |
| 4,513,745 A | 4/1985 | Amoils | |
| 4,530,356 A | 7/1985 | Helfgott et al. | |
| 4,533,818 A | 8/1985 | Green | |
| 4,549,554 A | 10/1985 | Markham | |
| 4,562,838 A | 1/1986 | Walker | |
| 4,570,632 A | 2/1986 | Woods | |
| 4,594,073 A | 6/1986 | Stine | |
| 4,600,014 A | 7/1986 | Beraha | |
| 4,605,011 A | 8/1986 | Naslund | |
| 4,644,951 A | 2/1987 | Bays | |
| 4,651,753 A | 3/1987 | Lifton | |
| 4,667,684 A | 5/1987 | Leigh | |
| 4,696,298 A | 9/1987 | Higgins et al. | |
| 4,697,600 A | 10/1987 | Cardenas et al. | |
| 4,699,154 A | 10/1987 | Lindgren | |
| 4,708,147 A | 11/1987 | Haaga | |
| 4,711,250 A | 12/1987 | Gilbaugh, Jr. et al. | |
| 4,733,671 A | 3/1988 | Mehl | |
| 4,735,215 A * | 4/1988 | Goto et al. | 600/567 |
| 4,747,414 A | 5/1988 | Brossel | |
| 4,776,346 A | 10/1988 | Beraha et al. | |
| 4,776,840 A | 10/1988 | Freitas et al. | |
| 4,781,700 A | 11/1988 | Vicario | |
| 4,803,341 A | 2/1989 | Barowski et al. | |
| 4,817,631 A | 4/1989 | Schnepp-Pesch et al. | |
| 4,850,373 A | 7/1989 | Zatloukal et al. | |
| 4,871,074 A | 10/1989 | Bryson et al. | |
| 4,881,551 A | 11/1989 | Taylor | |
| 4,893,635 A * | 1/1990 | de Groot et al. | 600/567 |
| 4,907,598 A | 3/1990 | Bauer | |
| 4,919,146 A | 4/1990 | Rhinehart et al. | |
| 4,926,877 A | 5/1990 | Bookwalter | |
| RE33,258 E | 7/1990 | Onik et al. | |
| 4,950,265 A | 8/1990 | Taylor | |
| 4,973,019 A | 11/1990 | Baird et al. | |
| 4,982,739 A | 1/1991 | Hemstreet et al. | |
| 4,985,027 A | 1/1991 | Dressel | |
| 4,989,614 A | 2/1991 | Dejter, Jr. et al. | |
| 5,019,036 A | 5/1991 | Stahl | |
| 5,025,797 A | 6/1991 | Baran | |
| 5,027,827 A | 7/1991 | Cody et al. | |
| 5,031,778 A | 7/1991 | Edgecombe | |
| 5,048,538 A | 9/1991 | Terwilliger et al. | |
| 5,054,615 A | 10/1991 | Stillwagon et al. | |
| 5,074,311 A | 12/1991 | Hasson | |
| 5,090,649 A | 2/1992 | Tipp | |
| 5,124,532 A | 6/1992 | Hafey et al. | |
| 5,125,413 A * | 6/1992 | Baran | 600/567 |
| 5,127,419 A * | 7/1992 | Kaldany | 600/567 |
| 5,133,360 A | 7/1992 | Spears | |
| 5,141,189 A | 8/1992 | Andrew | |
| D329,304 S | 9/1992 | Tipp | |
| 5,159,933 A * | 11/1992 | Hut | 600/566 |
| 5,172,701 A | 12/1992 | Leigh | |
| D332,670 S | 1/1993 | McFarland | |
| 5,183,052 A | 2/1993 | Terwilliger | |
| 5,188,118 A | 2/1993 | Terwilliger | |
| 5,213,110 A * | 5/1993 | Kedem et al. | 600/567 |
| 5,220,926 A | 6/1993 | Jones | |
| 5,224,470 A * | 7/1993 | Schnepp-Pesch et al. | 600/566 |
| 5,246,011 A | 9/1993 | Caillouette | |
| 5,249,582 A | 10/1993 | Taylor | |
| D342,585 S | 12/1993 | Fischbach et al. | |
| 5,275,609 A | 1/1994 | Pingleton et al. | |
| 5,281,197 A | 1/1994 | Arias et al. | |
| 5,282,476 A | 2/1994 | Terwilliger | |
| 5,285,795 A | 2/1994 | Ryan et al. | |
| 5,289,831 A | 3/1994 | Bosley | |
| 5,295,890 A | 3/1994 | Ersek | |
| 5,295,980 A | 3/1994 | Ersek | |
| 5,312,354 A * | 5/1994 | Allen et al. | 604/157 |
| 5,348,022 A | 9/1994 | Leight et al. | |
| 5,374,252 A | 12/1994 | Banks et al. | |
| 5,400,798 A * | 3/1995 | Baran | 600/567 |
| 5,403,276 A | 4/1995 | Schechter et al. | |
| 5,411,513 A | 5/1995 | Ireland et al. | |
| 5,423,844 A | 6/1995 | Miller | |
| 5,425,376 A * | 6/1995 | Banys et al. | 600/566 |
| 5,429,138 A | 7/1995 | Jamshidi | |
| 5,456,267 A | 10/1995 | Stark | |
| 5,458,112 A | 10/1995 | Weaver | |
| 5,464,300 A | 11/1995 | Crainich | |
| 5,469,860 A | 11/1995 | De Santis | |
| 5,492,130 A | 2/1996 | Chiou | |
| 5,505,211 A | 4/1996 | Ohto et al. | |
| 5,507,298 A * | 4/1996 | Schramm et al. | 600/567 |
| 5,511,556 A | 4/1996 | DeSantis | |
| 5,520,635 A | 5/1996 | Gelbfish | |
| D371,220 S | 6/1996 | Behrens | |
| 5,526,822 A | 6/1996 | Burbank et al. | |
| 5,535,755 A | 7/1996 | Heske | |
| 5,546,957 A * | 8/1996 | Heske | 600/567 |
| 5,560,373 A * | 10/1996 | De Santis | 600/566 |
| 5,575,293 A | 11/1996 | Miller et al. | |
| 5,580,347 A | 12/1996 | Reimels | |
| D377,996 S | 2/1997 | Gilbert | |
| 5,615,782 A | 4/1997 | Choe | |
| D379,554 S | 5/1997 | Landers | |
| 5,643,304 A | 7/1997 | Schechter et al. | |
| 5,649,547 A | 7/1997 | Ritchart et al. | |
| 5,669,876 A | 9/1997 | Schechter et al. | |
| 5,669,923 A | 9/1997 | Gordon | |
| D386,818 S | 11/1997 | Boomfield | |
| 5,685,840 A | 11/1997 | Schechter et al. | |
| 5,730,717 A | 3/1998 | Gelbfish | |
| 5,769,086 A | 6/1998 | Ritchart et al. | |
| 5,775,333 A | 7/1998 | Burbank et al. | |
| 5,782,849 A | 7/1998 | Miller | |
| 5,788,651 A | 8/1998 | Weilandt | |
| 5,794,626 A | 8/1998 | Kieturakis | |
| 5,794,799 A | 8/1998 | Collins et al. | |
| 5,797,907 A | 8/1998 | Clement | |
| 5,810,806 A | 9/1998 | Ritchart et al. | |
| 5,817,033 A | 10/1998 | DeSantis et al. | |
| 5,843,111 A | 12/1998 | Vijfvinkel | |
| 5,848,978 A | 12/1998 | Cecchi | |
| D403,810 S | 1/1999 | Owens | |
| 5,893,862 A | 4/1999 | Pratt et al. | |
| 5,911,701 A | 6/1999 | Miller et al. | |
| 5,913,857 A | 6/1999 | Ritchart et al. | |
| 5,916,229 A | 6/1999 | Evans | |
| 5,928,164 A | 7/1999 | Burbank et al. | |
| 5,928,218 A | 7/1999 | Gelbfish | |
| 5,944,673 A | 8/1999 | Gregoire et al. | |

| | | | |
|---|---|---|---|
| 5,964,716 A | 10/1999 | Gregoire et al. | |
| 5,971,939 A | 10/1999 | DeSantis et al. | |
| 5,980,469 A * | 11/1999 | Burbank et al. | 600/567 |
| 5,980,545 A | 11/1999 | Pacala et al. | |
| 5,980,546 A | 11/1999 | Hood | |
| 5,993,399 A | 11/1999 | Pruitt et al. | |
| 5,997,560 A | 12/1999 | Miller | |
| 6,007,497 A | 12/1999 | Huitema | |
| 6,017,316 A * | 1/2000 | Ritchart et al. | 600/567 |
| 6,019,733 A | 2/2000 | Farasconi | |
| 6,022,324 A | 2/2000 | Skinner | |
| D423,717 S | 4/2000 | Taylor | |
| 6,050,955 A | 4/2000 | Bryan et al. | |
| D426,025 S | 5/2000 | Holmes et al. | |
| 6,059,807 A | 5/2000 | Boudjema | |
| 6,077,230 A | 6/2000 | Gregoire et al. | |
| 6,080,113 A | 6/2000 | Heneveld et al. | |
| 6,085,749 A | 7/2000 | Wardle et al. | |
| 6,086,544 A | 7/2000 | Hibner et al. | |
| 6,096,042 A | 8/2000 | Herbert | |
| 6,109,446 A | 8/2000 | Foote | |
| 6,120,462 A | 9/2000 | Hibner et al. | |
| 6,120,463 A | 9/2000 | Bauer | |
| 6,123,299 A | 9/2000 | Zach, Sr. | |
| 6,142,955 A | 11/2000 | Farascioni et al. | |
| 6,155,989 A * | 12/2000 | Collins | 600/565 |
| 6,161,034 A | 12/2000 | Burbank et al. | |
| 6,162,187 A | 12/2000 | Buzzard et al. | |
| 6,193,414 B1 | 2/2001 | Balzano | |
| 6,193,673 B1 | 2/2001 | Viola et al. | |
| 6,251,418 B1 | 6/2001 | Ahern et al. | |
| 6,258,064 B1 | 7/2001 | Smith et al. | |
| 6,273,862 B1 | 8/2001 | Privitera et al. | |
| 6,280,399 B1 | 8/2001 | Rossin et al. | |
| 6,293,957 B1 | 9/2001 | Peters et al. | |
| 6,346,107 B1 | 2/2002 | Cucin | |
| 6,347,241 B2 | 2/2002 | Burbank et al. | |
| 6,358,217 B1 * | 3/2002 | Bourassa | 600/567 |
| 6,387,057 B1 | 5/2002 | Heske | |
| 6,402,701 B1 | 6/2002 | Kaplan et al. | |
| 6,419,641 B1 | 7/2002 | Mark et al. | |
| 6,428,486 B2 | 8/2002 | Ritchart et al. | |
| 6,436,054 B1 | 8/2002 | Viola et al. | |
| 6,461,350 B1 | 10/2002 | Underwood et al. | |
| 6,468,225 B1 | 10/2002 | Lundgren | |
| 6,468,227 B2 | 10/2002 | Zimmon | |
| 6,485,436 B1 | 11/2002 | Truckai et al. | |
| 6,488,636 B2 * | 12/2002 | Bryan et al. | 600/566 |
| 6,494,844 B1 | 12/2002 | Van Bladel et al. | |
| 6,506,165 B1 | 1/2003 | Sweeney | |
| 6,514,215 B1 | 2/2003 | Ouchi | |
| 6,551,255 B2 | 4/2003 | Van Bladel et al. | |
| 6,554,778 B1 | 4/2003 | Fleming, III | |
| 6,554,779 B2 * | 4/2003 | Viola et al. | 600/568 |
| 6,572,563 B2 | 6/2003 | Ouchi | |
| 6,589,240 B2 | 7/2003 | Hinchliffe | |
| 6,592,530 B1 * | 7/2003 | Farhadi | 600/564 |
| 6,626,868 B1 | 9/2003 | Prestidge et al. | |
| 6,632,182 B1 | 10/2003 | Treat | |
| 6,702,760 B2 * | 3/2004 | Krause et al. | 600/564 |
| 6,712,773 B1 | 3/2004 | Viola | |
| 6,725,083 B1 | 4/2004 | Burbank et al. | |
| 6,863,676 B2 | 3/2005 | Lee et al. | |
| 6,942,627 B2 * | 9/2005 | Huitema | 600/566 |
| 6,997,926 B2 | 2/2006 | Gellman et al. | |
| 7,278,970 B2 | 10/2007 | Goldenberg | |
| 7,390,306 B2 * | 6/2008 | Mark | 600/566 |
| 7,458,940 B2 * | 12/2008 | Miller | 600/568 |
| 7,608,048 B2 | 10/2009 | Goldenberg | |
| 2001/0014785 A1 | 8/2001 | Sussman et al. | |
| 2002/0111563 A1 | 8/2002 | Hall | |
| 2003/0018281 A1 * | 1/2003 | Huitema | 600/567 |
| 2003/0125639 A1 | 7/2003 | Fisher et al. | |
| 2003/0153874 A1 | 8/2003 | Tal | |
| 2003/0195436 A1 | 10/2003 | Van Bladel et al. | |
| 2003/0229293 A1 | 12/2003 | Hibner et al. | |
| 2004/0019297 A1 * | 1/2004 | Angel | 600/564 |
| 2004/0082915 A1 * | 4/2004 | Kadan | 604/164.04 |
| 2004/0097830 A1 | 5/2004 | Cooke et al. | |
| 2004/0158172 A1 * | 8/2004 | Hancock | 600/564 |
| 2004/0162572 A1 | 8/2004 | Sauer | |
| 2004/0230133 A1 | 11/2004 | Miller et al. | |
| 2005/0027210 A1 | 2/2005 | Miller | |
| 2005/0054947 A1 | 3/2005 | Goldenberg | |
| 2005/0075580 A1 * | 4/2005 | Leigh et al. | 600/567 |
| 2005/0080355 A1 | 4/2005 | Mark | |
| 2005/0165328 A1 | 7/2005 | Heske et al. | |
| 2005/0203439 A1 * | 9/2005 | Heske et al. | 600/566 |
| 2005/0240118 A1 * | 10/2005 | Huitema | 600/566 |
| 2005/0277829 A1 * | 12/2005 | Tsonton et al. | 600/423 |
| 2006/0089565 A1 | 4/2006 | Schramm | |
| 2006/0155210 A1 | 7/2006 | Beckman et al. | |
| 2006/0173377 A1 | 8/2006 | McCullough et al. | |
| 2007/0106176 A1 | 5/2007 | Mark et al. | |
| 2008/0154151 A1 * | 6/2008 | Ritchart et al. | 600/566 |
| 2008/0200835 A1 | 8/2008 | Monson et al. | |
| 2009/0204023 A1 | 8/2009 | Goldenberg | |

FOREIGN PATENT DOCUMENTS

| | | |
|---|---|---|
| DE | 20204363 | 5/2002 |
| EP | 0 010 321 | 4/1980 |
| EP | 0561732 | 9/1993 |
| EP | 1520518 A2 | 4/2005 |
| EP | 1 698 283 A1 | 9/2006 |
| SU | 1551362 | 1/1987 |
| WO | WO-83/03343 | 10/1983 |
| WO | WO-9624289 A | 8/1996 |
| WO | WO-9720504 | 6/1997 |
| WO | WO-02/22023 A1 | 3/2002 |
| WO | WO-0222023 A | 3/2002 |
| WO | WO-03/009766 A1 | 2/2003 |
| WO | WO03/066676 * | 9/2003 |
| WO | WO-2005037106 A | 4/2005 |
| WO | WO-2005063126 A | 7/2005 |
| WO | WO-2006/083770 A2 | 8/2006 |
| WO | WO-2008106583 A1 | 9/2008 |

OTHER PUBLICATIONS

U.S. Appl. No. 12/124,949, filed May 21, 2008.
U.S. Appl. No. 12/205,291, filed Sep. 5, 2008.
U.S. Appl. No. 60/510,866, filed Oct. 14, 2003.
U.S. Appl. No. 60/892,174, filed Feb. 28, 2007.
U.S. Appl. No. 60/970,770, filed Sep. 7, 2007.
International Search Report No. PCT/US01/51235 dated Dec. 10, 2002.
Publication in Design News entitled "Probe reduces breast biopsy trauma" by Joseph Ogando dated Aug. 7, 2000.
Steven K. Wagner, "Imaging News," Breast ultrasound spurs biopsy technology race, (Mar. 6, 1996).
CA Publication in Design News entitled "Probe reduces breast biopsy trauma" by Joseph Ogando dated Aug. 7, 2000.
International Search Report No. PCT/US01/51235.
Publication in OBGYN.net entitled "Minimally Invsive Surgery Products for General Surgery Continue to Provide Opportunities for Innovative Manufacturers" by Keith Hammond, dated Apr. 22, 1998.
International Search Report No. PCT/US2004/033909 dated May 18, 2005.
Publication in OBGYN.net entitled "Minimally Invsive Surgery Products for General Surgery Continue to Provide Opportunities for Innovative Manufacturers" by Keith Hammond.
PCT International Search Report PCT/IB2007/050975 dated Nov. 21, 2007.
International Search Report for PCT/US2008/055248 dated Jun. 17, 2008.
Non-Final Office Action dated Apr. 15, 2009 for U.S. Appl. No. 11/389,274.
Amendment in Response to Non-Final Office Action for U.S. Appl. No. 11/389,274 dated Jul. 13, 2009.
Office Action dated Nov. 30, 2009 for U.S. Appl. No. 11/389,274.
Article entitled "Diagnosis of non-palpable breast cancer; a review" by M.F. Ernst and J.A. Roukema; The Breast (2002 Harcourt Publishers Ltd.).
Brochure entitled "Interventional MRI"; Invivo Corporation Daum Technology; Copyright 2005.

International Search Report for PCT/US2009/049214 dated Sep. 15, 2009.
Response to Office Action dated Nov. 30, 2009 for U.S. Appl. No. 11/389,274.
Non-Final Office Action dated May 14, 2010 for U.S. Appl. No. 12/124,949.
Response to Non-Final Office Action datd May 14, 2010 for U.S. Appl. No. 12/124,949.
Final Office Action issued Jun. 9, 2010 for U.S. Appl. No. 11/389,274.
Response to Final Office Action dated Jun. 9, 2010 for U.S. Appl. No. 11/389,274.
Final Office action dated Oct. 26, 2010 for U.S. Appl. No. 12/124,949.
Response to Final Office Action dated Oct. 26, 2010 for U.S. Appl. No. 12/124,949.
Non-Final Office Action dated Feb. 4, 2011 for U.S. Appl. No. 11/389,274.
Notice of Allowance dated Mar. 8, 2011 for U.S. Appl. No. 12/039,364.
Reponse to Non-Final Office Action dated Feb. 4, 2011 for U.S. Appl. No. 11/389,274.
Final Office Action dated Jun. 8, 2011 for U.S. Appl. No. 12/124,949.
Final Office Action dated Jul. 21, 2011 for U.S. Appl. No. 11/389,274.

* cited by examiner

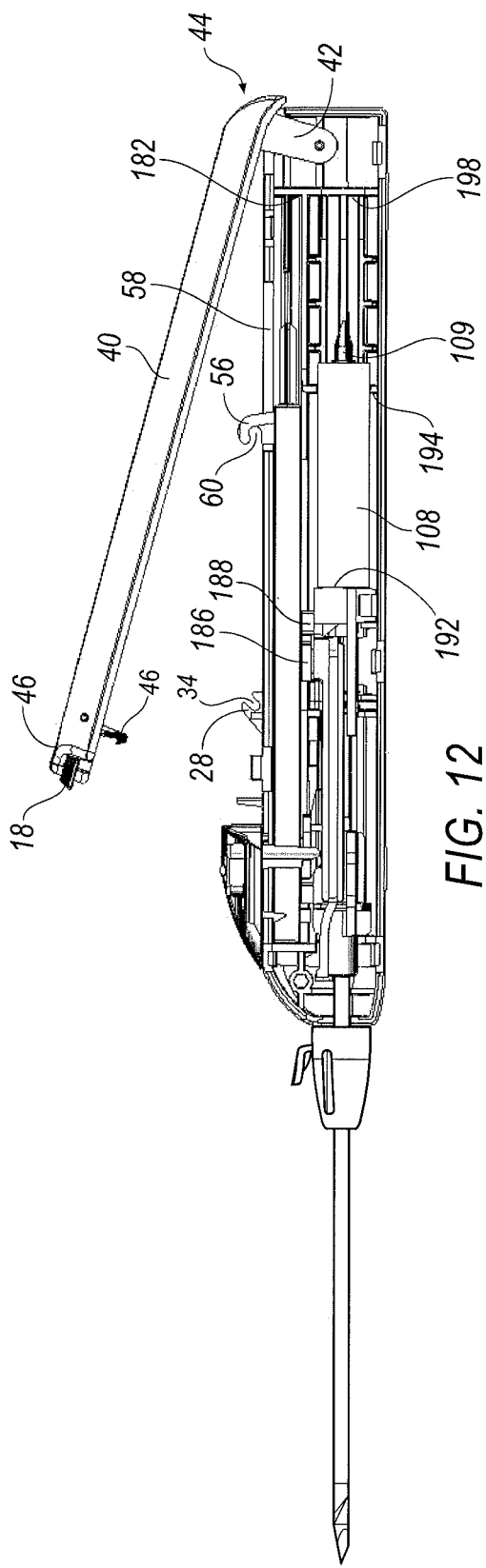
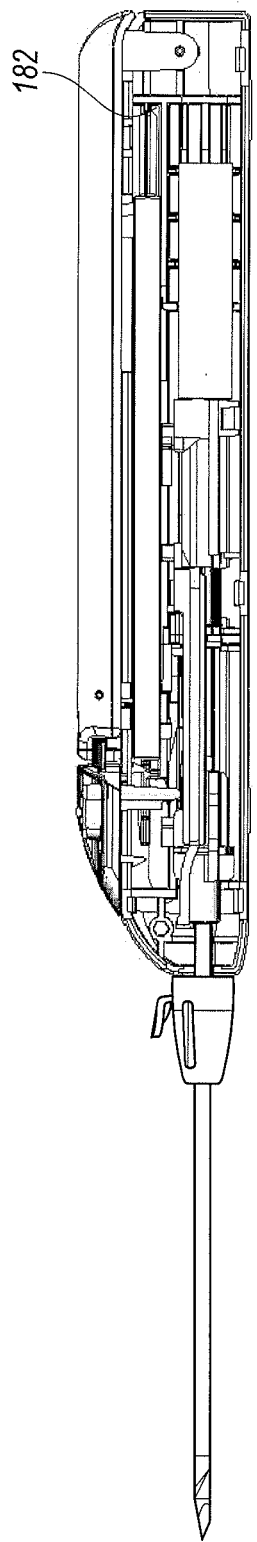

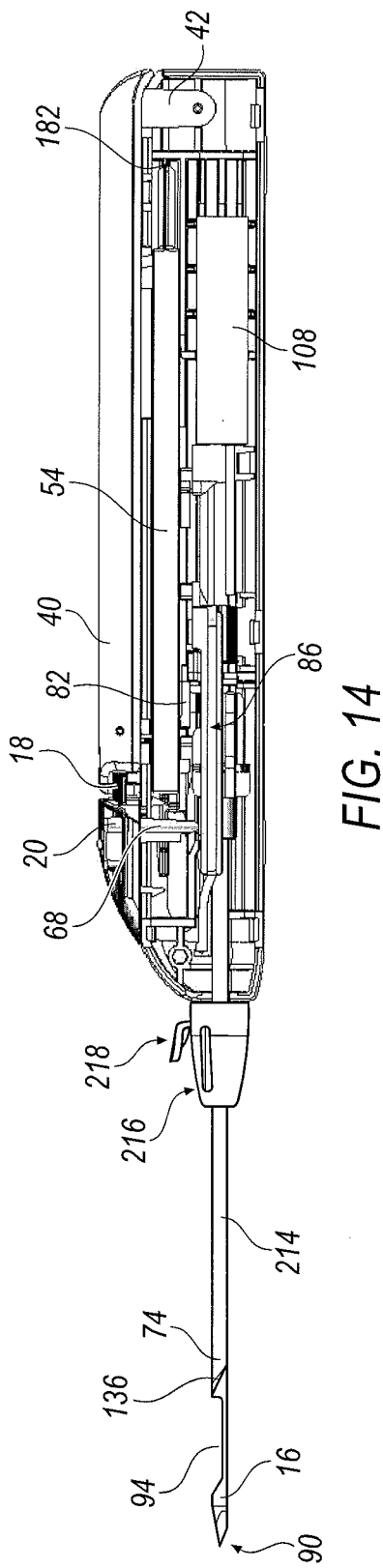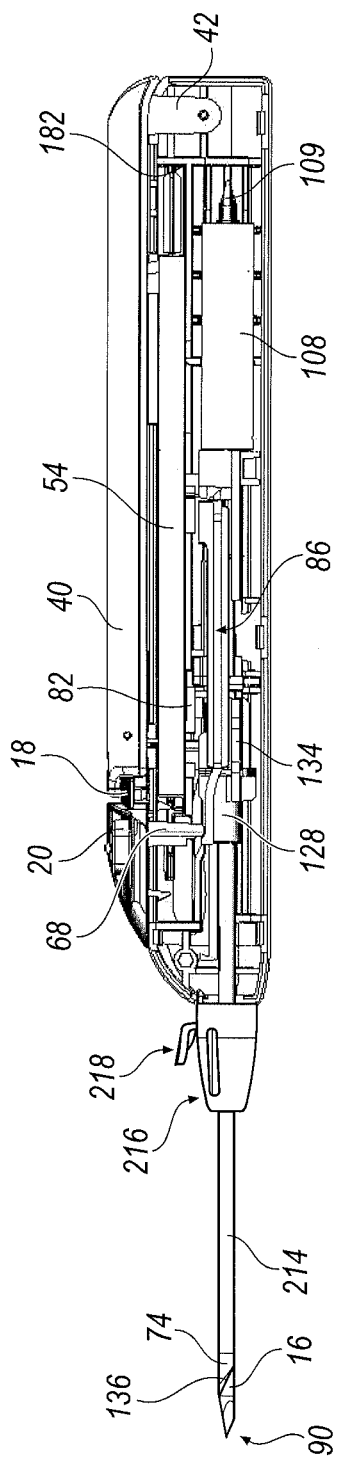

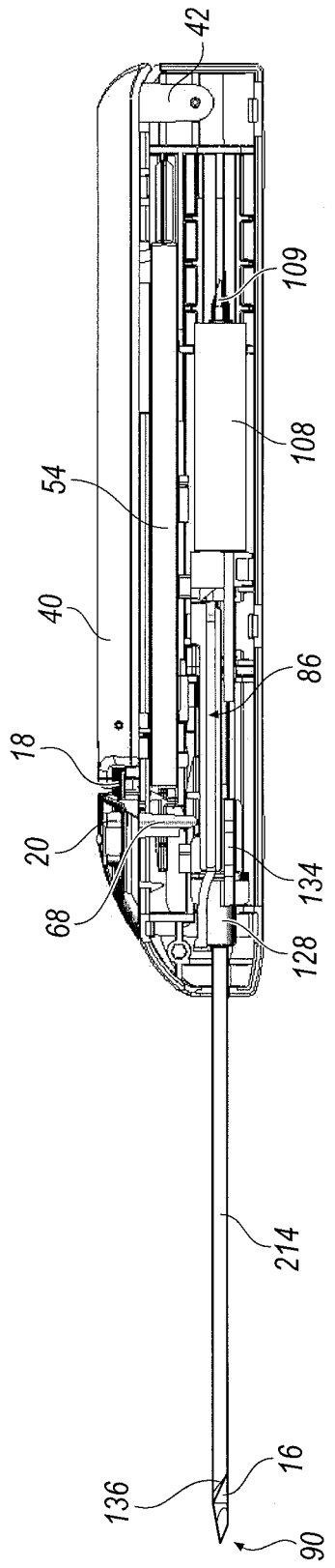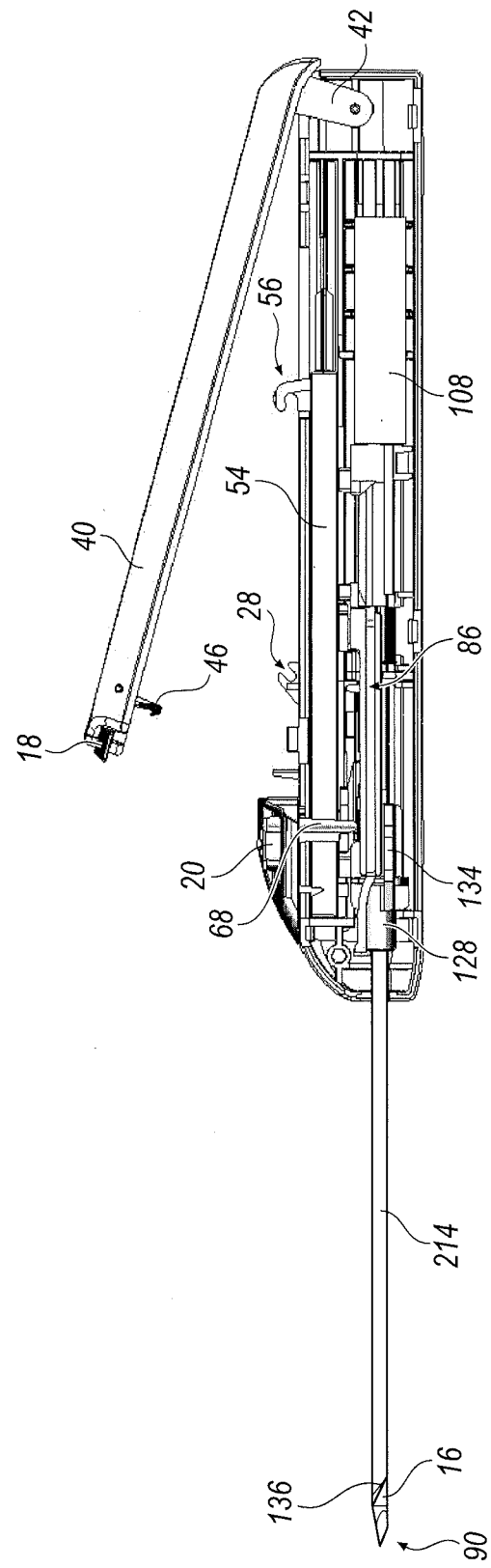

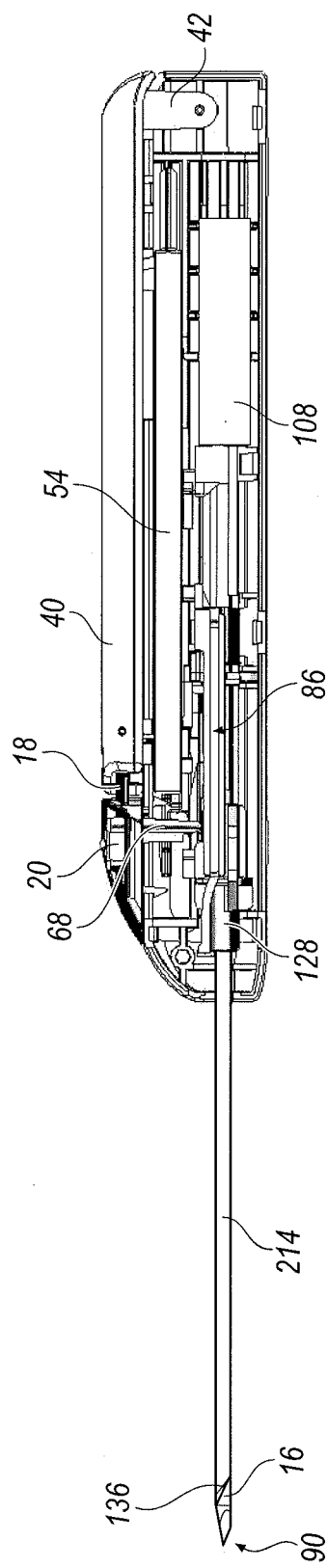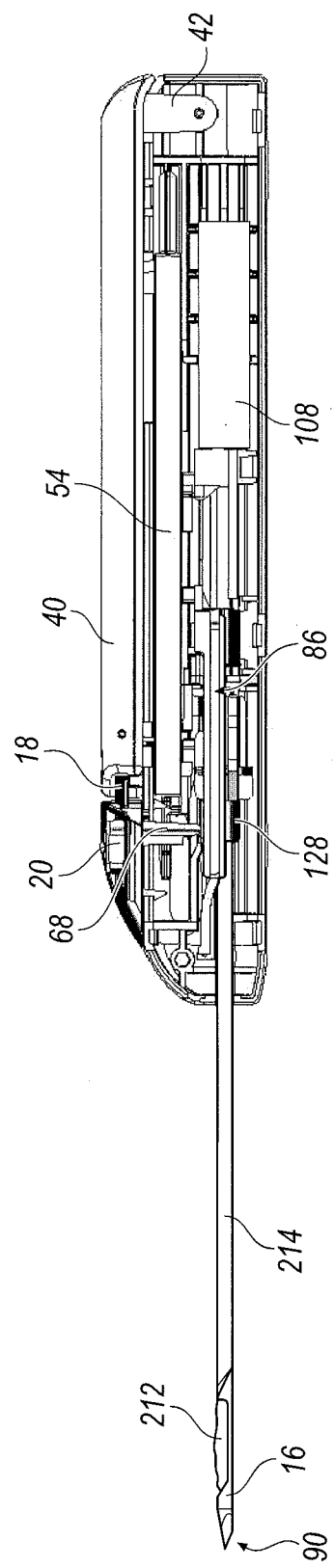

VACUUM ASSISTED BIOPSY DEVICE

CROSS-REFERENCE TO RELATED APPLICATIONS

This application is a Continuation application of U.S. Ser. No. 12/205,291 filed Sep. 5, 2008 now U.S. Pat. No. 8,048,003, which claims priority to U.S. Provisional App. Ser. No. 60/970,770 filed on Sep. 7, 2007, and is a Continuation-in-part of U.S. Ser. No. 12/039,364, Feb. 28, 2008 now U.S. Pat. No. 7,988,642 issued on Aug. 2, 2011, which claims priority to U.S. Provisional patent application Ser. No. 60/892,174, filed on Feb. 28, 2007 and which is a Continuation-in-part of U.S. Ser. No. 11/389,274 filed on Mar. 24, 2006, now U.S. Pat. No. 8,357,103 which is a Continuation-in-Part of U.S. Ser. No. 10/964,959 filed Oct. 14, 2004, now U.S. Pat. No. 7,390,306 issued on Jun. 24, 2008, which claims priority to U.S. provisional patent application Ser. No. 60/510,866 filed on Oct. 14, 2003, the disclosures of which are incorporated herein by reference in their entireties.

TECHNICAL FIELD

The present disclosure generally relates to the field of tissue sampling and harvesting. More specifically, the disclosure relates to biopsy needle sets and devices.

BACKGROUND

In the practice of diagnostic medicine, it is often necessary or desirable to perform a biopsy, or to sample selected tissue from a patient for medical evaluation. Cytological and histological studies of the biopsy sample can then be performed as an aid to the diagnosis and treatment of disease. Biopsies can be useful in diagnosing and treating various forms of cancer, as well as other diseases in which a localized area of affected tissue can be identified.

Biopsies are routinely performed on tissue using a needle set, which typically includes a stylet with a pointed tip and a notch defined near its distal end. The stylet is slidably disposed within a cannula so that the notch can be alternately exposed or covered. Such needle sets are used with or incorporated in various forms of biopsy devices, such as single action or double action biopsy devices.

More specifically, one known exemplary single action biopsy device includes a hollow needle. A stylet is slidingly disposed within the hollow needle lumen and is moveable relative to needle. A distal end of the stylet is provided with a tissue cutting-point and a tissue opening is positioned adjacent to the distal end for receiving tissue samples. The stylet is slidable relative to needle between a first or retracted position and a second or extended position.

In the first position, the stylet is retracted within the needle such that the needle covers the tissue opening. In the second position, the distal end of the stylet is extended away from the needle to expose the tissue opening to tissues at the biopsy site.

During a biopsy procedure, the device will be positioned within a cavity at a targeted site for the biopsy. The stylet is momentarily driven into the tissue and tissue then prolapses into the tissue opening. The needle is then advanced along the stylet to cover the tissue opening. This forward movement of needle severs the prolapsed tissue to obtain a tissue sample, which becomes trapped in tissue opening of the stylet. With the needle 22 blocking the opening of tissue opening, the biopsy device is then withdrawn from the target site, carrying the sample within tissue opening. To collect the biopsy sample, the needle is once again retracted to expose tissue opening of the stylet. The procedure may be repeated several times until satisfactory samples have been obtained.

While single and double action biopsy devices are widely used, a basic problem remains in the field of biopsy, which is the need to obtain a sufficient amount of sample tissue. One potential cause of the problem is that as the needle passes over the tissue opening, the needle has a tendency to push the tissue away from the tissue opening. This results in samples that are inferior in quality or too small, which precludes the pathologist from conclusively determining whether disease is present, and if so, to what extent it has progressed. The pathologist must then issue an inconclusive diagnostic report. This causes the physician to recall the patient and attempt another needle biopsy, or in some situations, the patient is scheduled for a more invasive, traumatic and expensive procedure such as an open surgical biopsy.

The challenge has been to consistently obtain sufficient tissue volume and quality tissue cores, regardless of tissue type, to meet the needs of the pathologist so that a conclusive diagnosis can be achieved.

SUMMARY

A biopsy device is disclosed that comprises a cutting element mounted to a handpiece and a vacuum chamber. The cutting element comprises a stylet assembly and an outer cannula assembly. The stylet assembly includes a stylet that includes an open proximal end and a tissue opening at a distal end thereof. The tissue receiving opening is in communication with a lumen extending through the stylet. The outer cannula assembly includes an outer cannula that is slidably mounted over the stylet and has an open distal end with a cutting edge formed thereon. The vacuum chamber is in communication with the lumen of the stylet. The stylet is selectively advanced distally outwardly with respect to outer cannula to expose the tissue opening to targeted tissue. The outer cannula is selectively advanced over the tissue opening to sever tissue, while vacuum is generated in the vacuum chamber and delivered to the tissue opening through the lumen. The vacuum causes tissue to be drawn into and maintained in the tissue opening while the outer cannula severs tissue to obtain a biopsy core. A method of using the biopsy device is also disclosed.

BRIEF DESCRIPTION OF THE DRAWINGS

Embodiments of the disclosure will now be described, by way of example, with reference to the accompanying drawings, wherein:

FIG. 12 is a partial cut-away side elevational view of the biopsy device after a release latch has been activated and an actuating lever has been released (note that the bridge member of FIG. 10 has been omitted for clarity).

FIG. 13 is a side elevational view of the biopsy device after the actuating lever has been depressed a first time, thereby retracting a piston.

FIG. 14 is a side elevational view of the biopsy device after the actuating lever has been depressed a second time, thereby retracting the cutting cannula.

FIG. 15 is a side elevational view of the biopsy device after the actuating lever has been depressed a third time, thereby retracting the stylet into the cutting cannula.

FIG. 17 is a side elevational view of the biopsy device after the cutting cannula has been fired forward over the tissue receiving opening of the stylet.

FIG. 18 is a side elevational view of the biopsy device after the release latch has been released (note that the bridge member of FIG. 10 has been omitted for clarity).

FIG. 19 is a side elevational view of the biopsy device after the vacuum chamber has been retracted.

FIG. 20 is a side elevational view of the biopsy device after the cutting cannula has been retracted so as to expose the tissue receiving opening to permit tissue cores to be removed from the tissue receiving opening.

DETAILED DESCRIPTION

Figure 1:
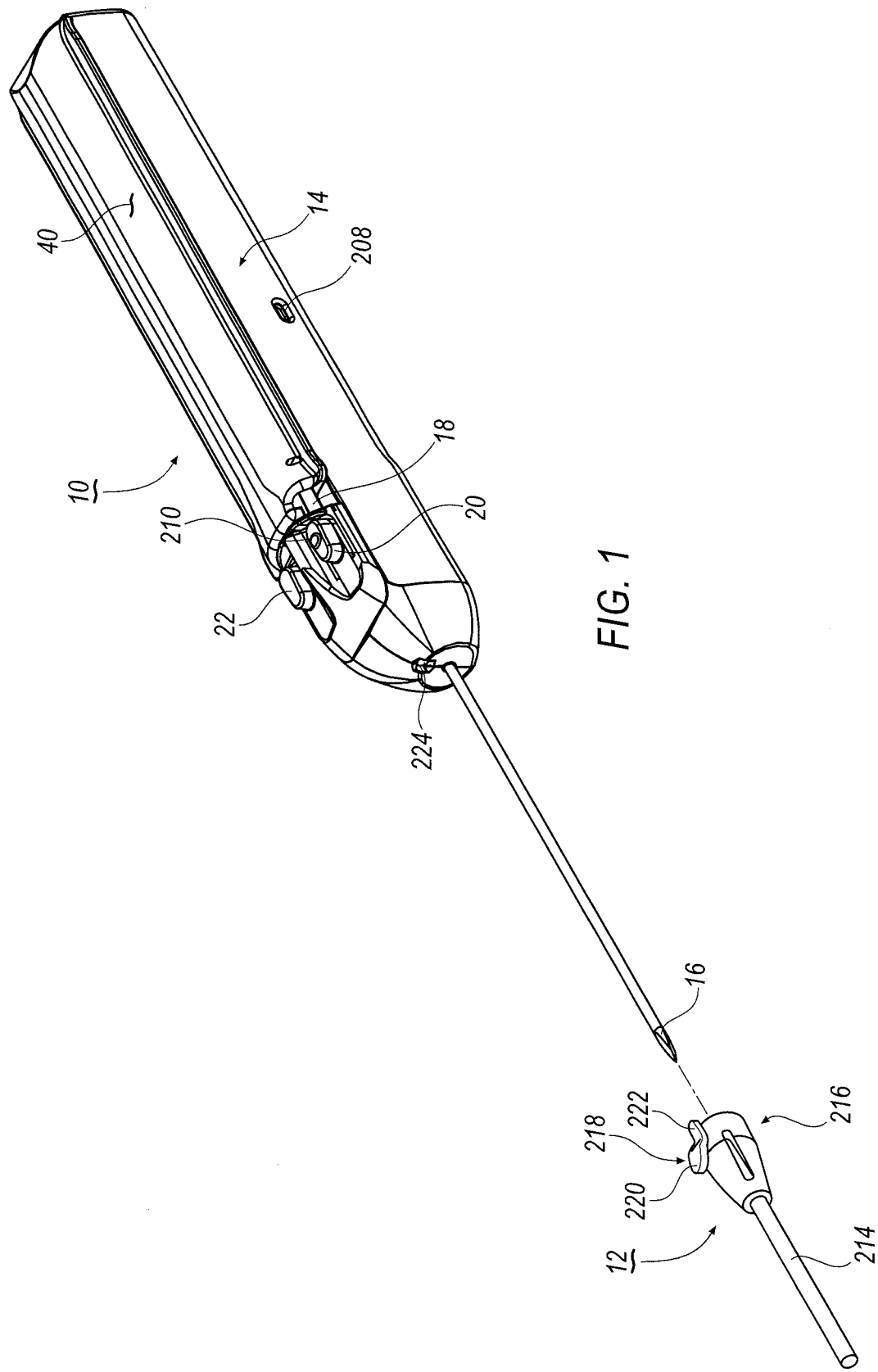
FIG. 1 is a perspective view of a biopsy device assembly, including a biopsy device and an introducer assembly.

Referring now to the drawings, preferred illustrative embodiments are shown in detail. Although the drawings represent some embodiments, the drawings are not necessarily to scale and certain features may be exaggerated, removed, or partially sectioned to better illustrate and explain the present disclosure. Further, the embodiments set forth herein are not intended to be exhaustive or otherwise limit or restrict the claims to the precise forms and configurations shown in the drawings and disclosed in the following detailed description.

Referring to FIG. 1, a perspective view of an exemplary biopsy device 10 in accordance with the present disclosure is illustrated. A separate and optional introducer assembly 12 is also illustrated.

As shown, biopsy device 10 is a handheld device and includes a housing 14 to which a stylet 16 is attached. Biopsy device 10 includes several release members 18, 20, and 22, to be explained in further detail below.

Figure 2:
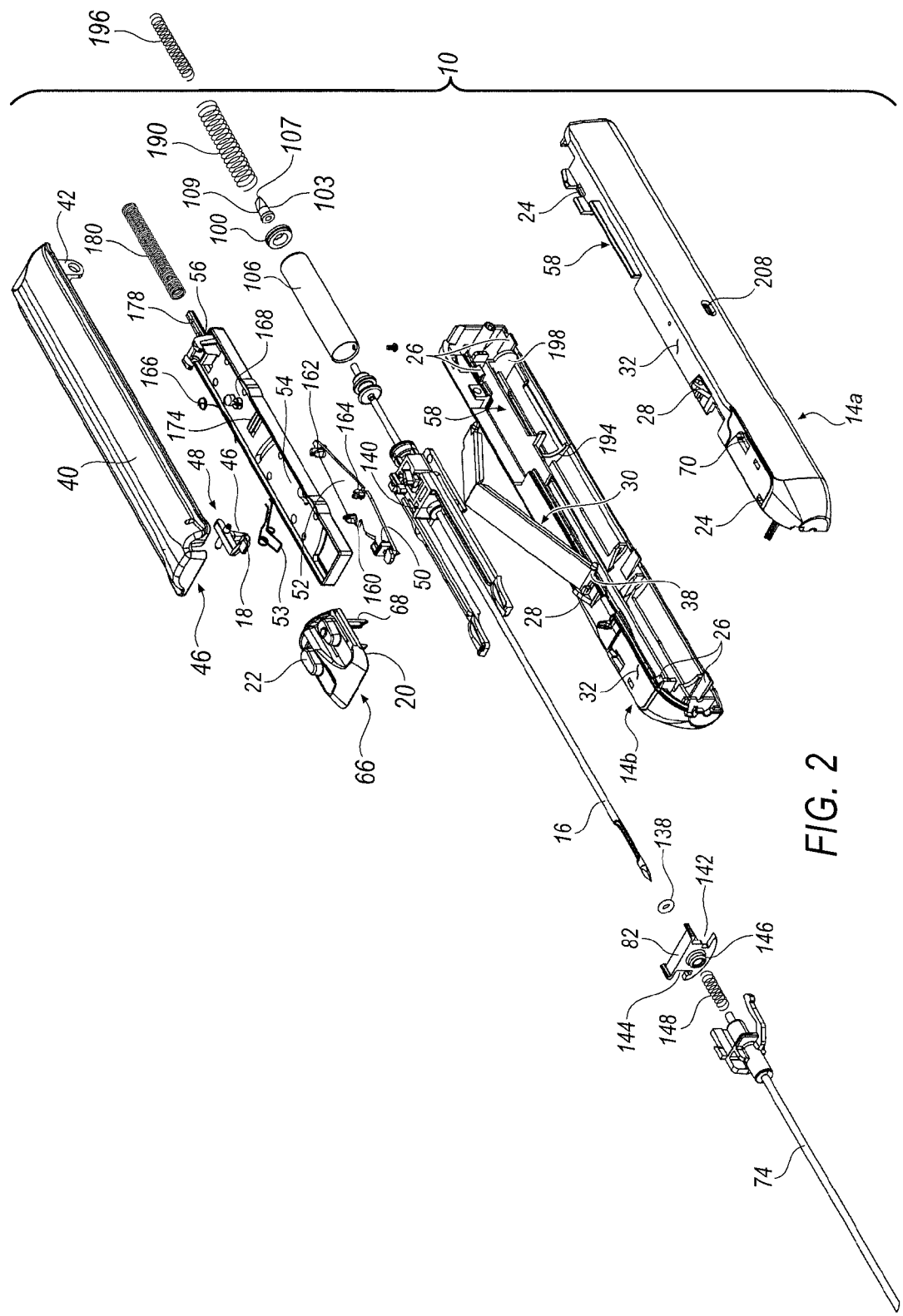
FIG. 2 is an exploded view of the biopsy device of FIG. 1.

Referring to FIG. 2, an exploded view of biopsy device 10 is illustrated. As shown, in the exemplary embodiment housing 14 is a two piece member, including a first housing member 14a and a second housing member 14b. In one embodiment, first and second housing members 14a and 14b are configured snap together to house actuation components of biopsy device 10. For example, first housing member 14a includes one or more slot members 24 positioned on top and bottom portions of first housing member 14a. Slot members 24 cooperate with and receive latch members 26 that are positioned on top and bottom portions of second housing member 14b. An interior of housing 14 is generally hollow to receive the actuation components.

While housing 14 has been described as snapping together, it is also understood that first and second housing members 14 may alternatively be secured together using fastening elements.

A top portion of each housing member 14a and 14b includes a holder 28 for securing a portion of a resilient bridge member 30. Each holder 28 extends upwardly from the top portion 32 and includes a groove 34 (best seen in FIG. 12) that receives mounting knobs 36 of a mounting member 38 positioned on a first end 35 of resilient bridge member 30.

Figure 4:
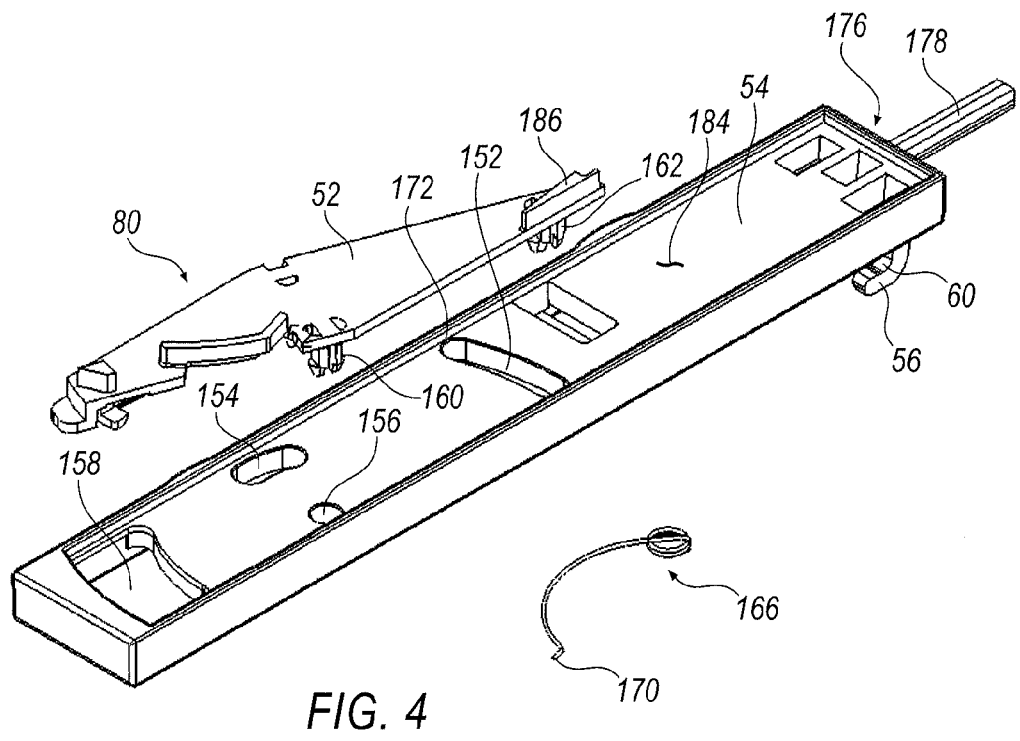
FIG. 4 is an exploded view of the pickup carriage assembly, illustrating a moveable cam member and a spring member that attaches to a top surface of the pickup carriage.
Figure 5:
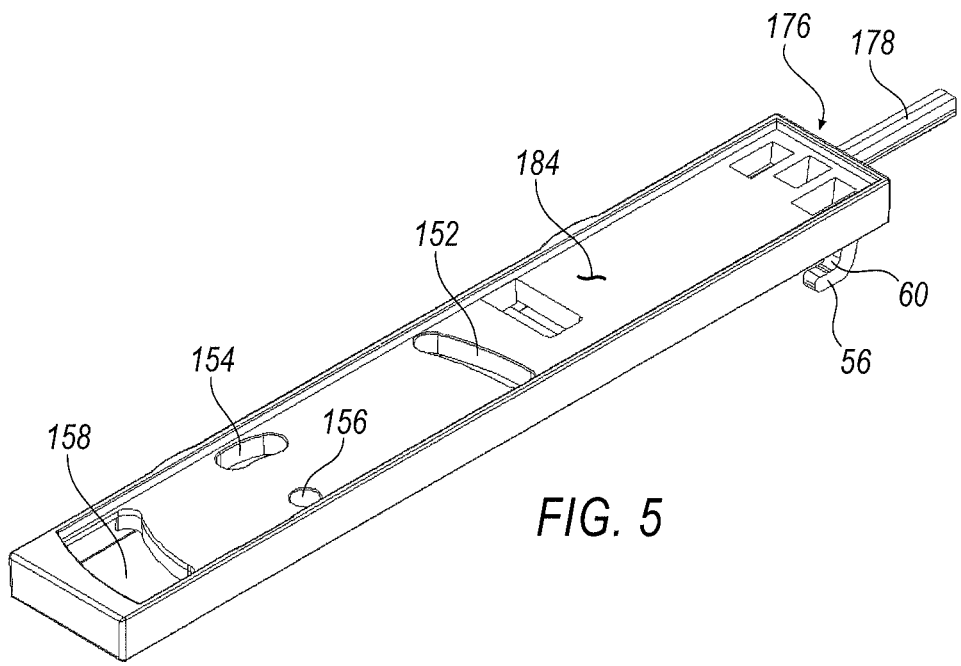
FIG. 5 is a perspective view of the underside of the pickup carriage.
Figure 6:
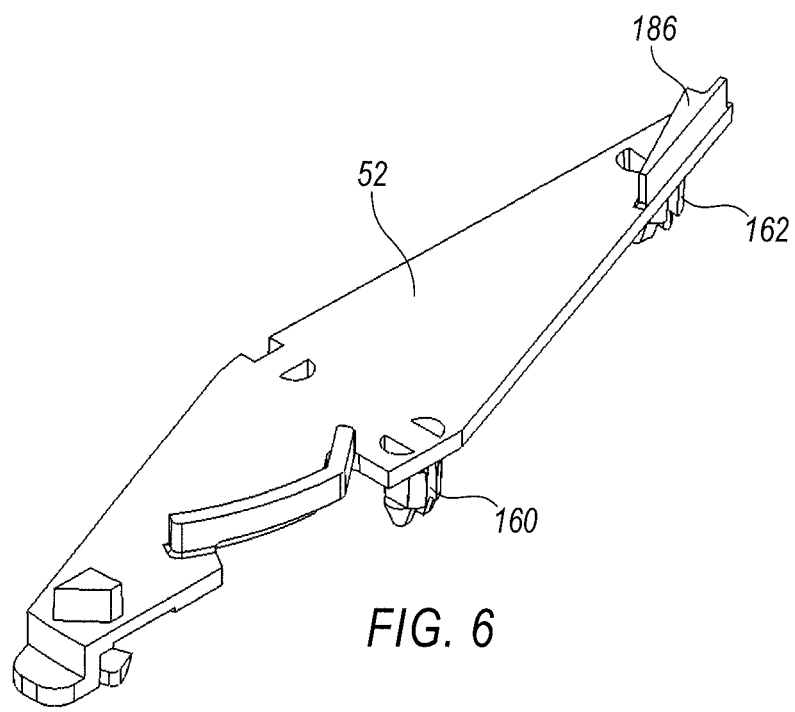
FIG. 6 is a perspective view of the moveable cam member.

An actuating lever 40 is pivotally attached to housing 14 by pivot arm 42 at a proximal end 44 of biopsy device 10. A forward end 46 of actuating lever 40 may rise upwardly from a top surface of housing 14 due to pivot arm 42. A lever release assembly 48 that carries a release mechanism 18 is attached to actuating lever 40. Lever release assembly 48 includes a downwardly extending latch arm 46 that selectively engages with a portion of a retaining member 50 disposed on a cam member 52 carried by a pickup carriage 54 (shown in FIGS. 3-5). A spring mechanism 53 serves to bias release mechanism 18 to an actuation position.

Pickup carriage 54 includes a pair of holders 56 that extend upwardly from a top surface thereof. Housing 14 includes an open channel 58 formed in the top surface thereof. When pickup carriage 54 is positioned within housing 14, holders 56 extend through channel 58 (seen in FIG. 12). Each holder 56 includes a groove 60 that receives a mounting knob 36 from a mounting member 38 positioned on a second end 62 of resilient bridge member 30.

Figure 10:
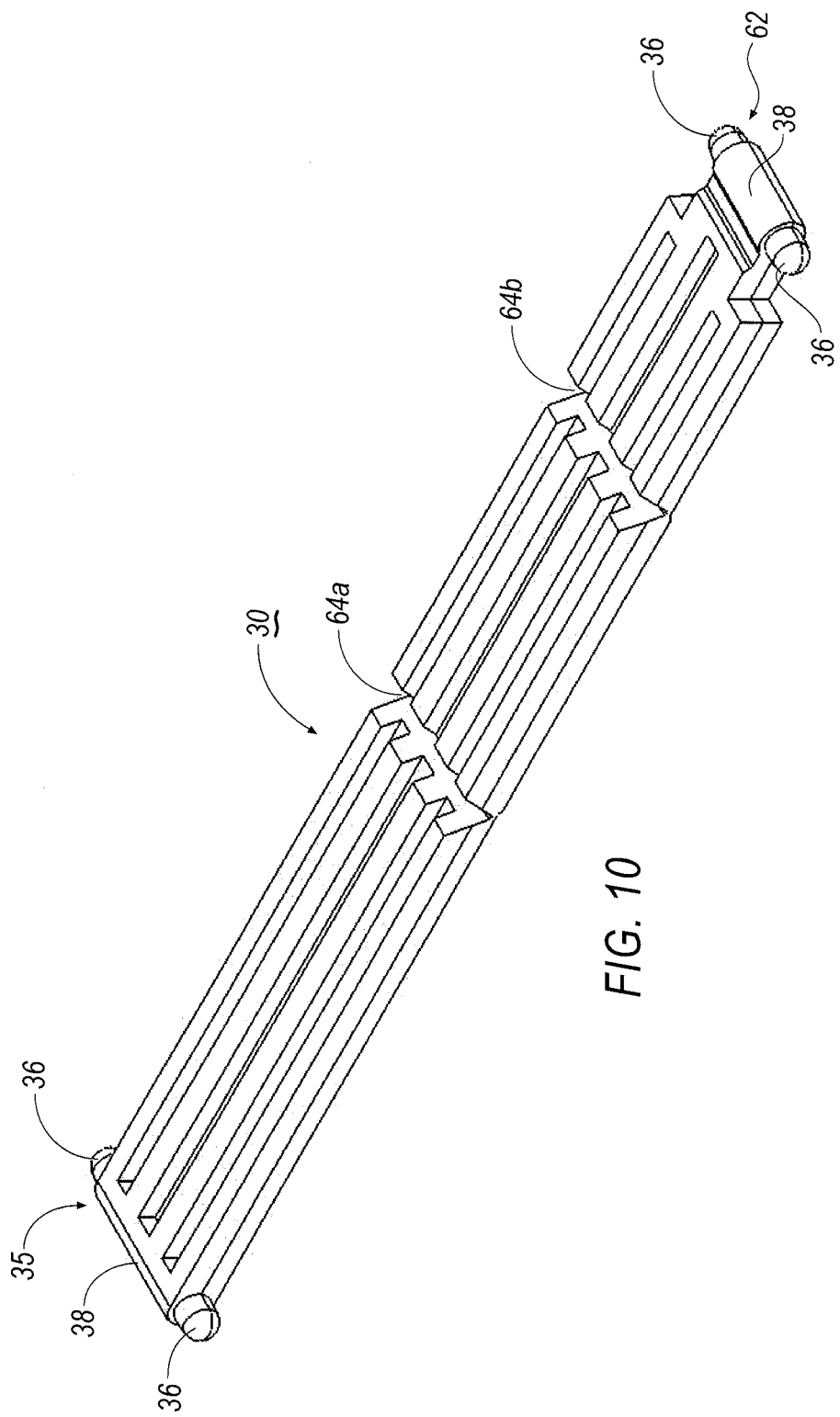
FIG. 10 is a perspective view of one embodiment of a resilient bridge member.

Referring to FIG. 10, resilient bridge member 30 includes a plurality of sections that are separated by hinge members 64a and 64b. Hinge members 64a and 64b are created by V-shaped notches that form thinned sections.

First end 35 of resilient bridge member 30 is secured to holders 28 and second end 62 is secured to holders 56 such that resilient bridge member 30 is positioned directly below actuation lever 40 when biopsy device 10 is assembled. Due to the configuration of resilient bridge member 30, when actuation lever 40 is depressed, actuation lever 40 pushes down on resilient bridge member 30. The pushing action flattens out resilient bridge member 30, thereby sliding pickup carriage member 54 away from a distal end of biopsy device 10.

Secured to a top portion of housing 14 is an actuation button carrier 66 that carries release mechanisms 20 and 22. Release mechanism 20 includes a downwardly extending latch arm 68 that extends downwardly into first housing member 14a though an opening 70 formed therein. As will be explained in further detail below, release mechanism 20 is actuated to release stylet 16. More specifically, an end of latch arm 68 is configured to grip a retaining arm 72 of stylet 16. When release mechanism 20 is depressed, the end of latch arm 68 is biased upwardly, thereby releasing its grip on retaining arm 72 of stylet 16 and permitting stylet to advance forward.

Release mechanism 22 also includes a downwardly extending latch arm (not shown). As will be explained n further detail below, the latch arm of release mechanism 22 releases an outer cutting cannula 74. More specifically, when release mechanism 22 is depressed, the end of the latch arm of release mechanism 22 is biased upwardly, thereby releasing outer cutting cannula 74 and permitting outer cannula 74 to advance forward.

Other components of biopsy device 10 includes a stylet assembly 76, an outer cannula assembly 78, a cam member assembly 80, a support rib 82, and a piston member 84. Each element will be discussed in turn below.

Figure 7:
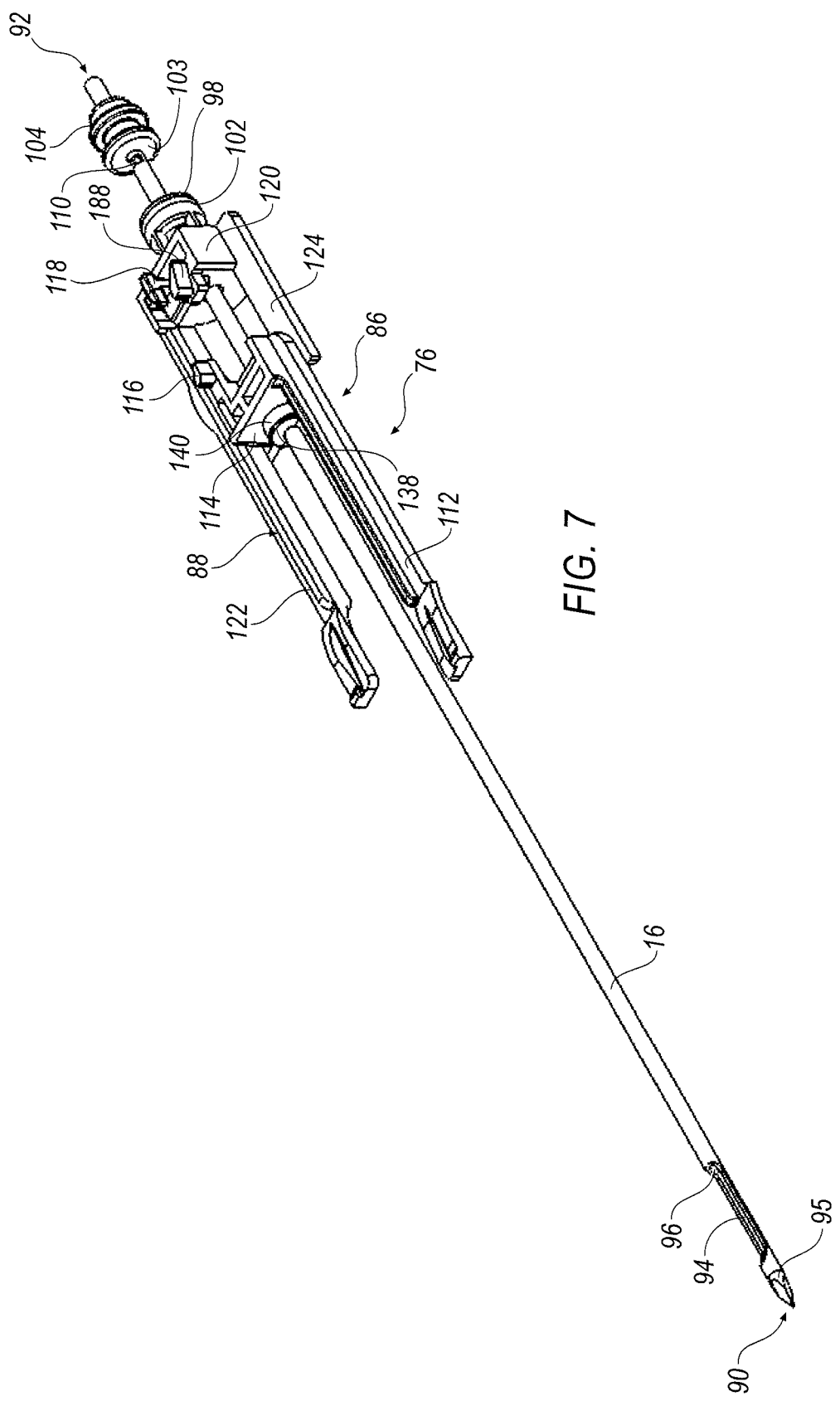
FIG. 7 is a perspective view of a stylet and vacuum hub assembly.
Figure 8:
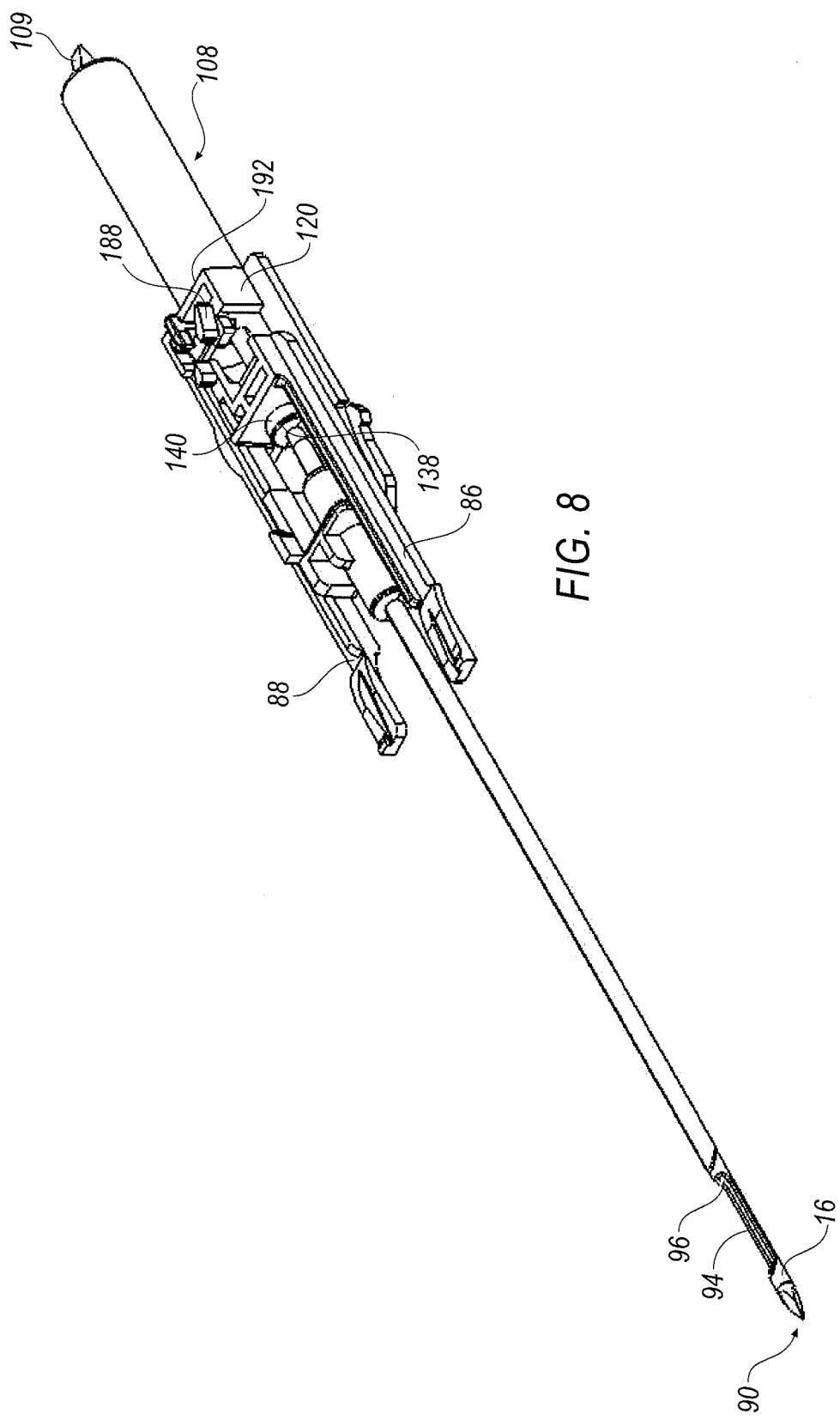
FIG. 8 is a perspective view of the stylet and vacuum hub assembly of FIG. 7 with a vacuum chamber enclosure member attached and a cutting cannula assembly attached.

Stylet assembly 76 is shown in FIG. 7. Stylet assembly 76 includes stylet 16, a first arm sub-assembly 86, and a second arm sub-assembly 88. Stylet 16 extends between a distal end 90 and an open proximal end 92. Adjacent distal end 90 is a tissue opening 94. Distal end 90 may further include a trocar piercing tip 95. Stylet assembly 76 further defines an inner lumen 96 that extends between tissue opening 94 and proximal end 92. Positioned adjacent proximal end 92 are first and second seal members 98, 100, respectively. First seal member 98 is attached to a first cap member 102 that is attached to second arm sub-assembly 88. Second seal member 100 positioned adjacent to a chamber wall member 103, which is positioned adjacent second end cap 104. Second end cap 104 is fixedly secured to stylet 16. Second seal member 100 (see FIG. 2) is disposed between first end cap 102 and chamber wall member 103. Thus, first end cap 102, chamber wall member 103, and first and second seal members 98, 100 cooperate with a cylinder 106 to define a vacuum chamber 108, to be explained in further detail below.

A notch 110 is cut into stylet 16, between first end cap 102 and chamber wall member 103. Notch 110 is in communication with inner lumen 96, which, in turn, is in communication with tissue opening 94. A one-way valve member 109 (to be discussed in further detail below) is attached to open proximal end 92 (see, e.g., FIG. 2).

First arm sub-assembly 86 is generally L-shaped and includes a leg member 112 and a carrier member 114. Carrier member 114 is fixedly secured to stylet 16. Carrier member 114 includes a fitting member 116 that cooperative engages a side of complimentary member 118 that is disposed on a carrier member 120 that is part of second arm sub-assembly 88.

Second arm sub-assembly 88 includes a long leg member 122 and a short leg member 124 that are connected together by carrier member 120. When assembled (and as best seen in FIG. 7), short leg member 124 is disposed beneath leg member 112 of first arm sub-assembly 86, with carrier member 114 being positioned above carrier member 120. First cap member 102 is attached to carrier member 120. First cap member 120 is fixedly secured to cylinder 106. Thus, as vacuum chamber 108 moves, so does second arm sub-assembly 88.

Figure 9:
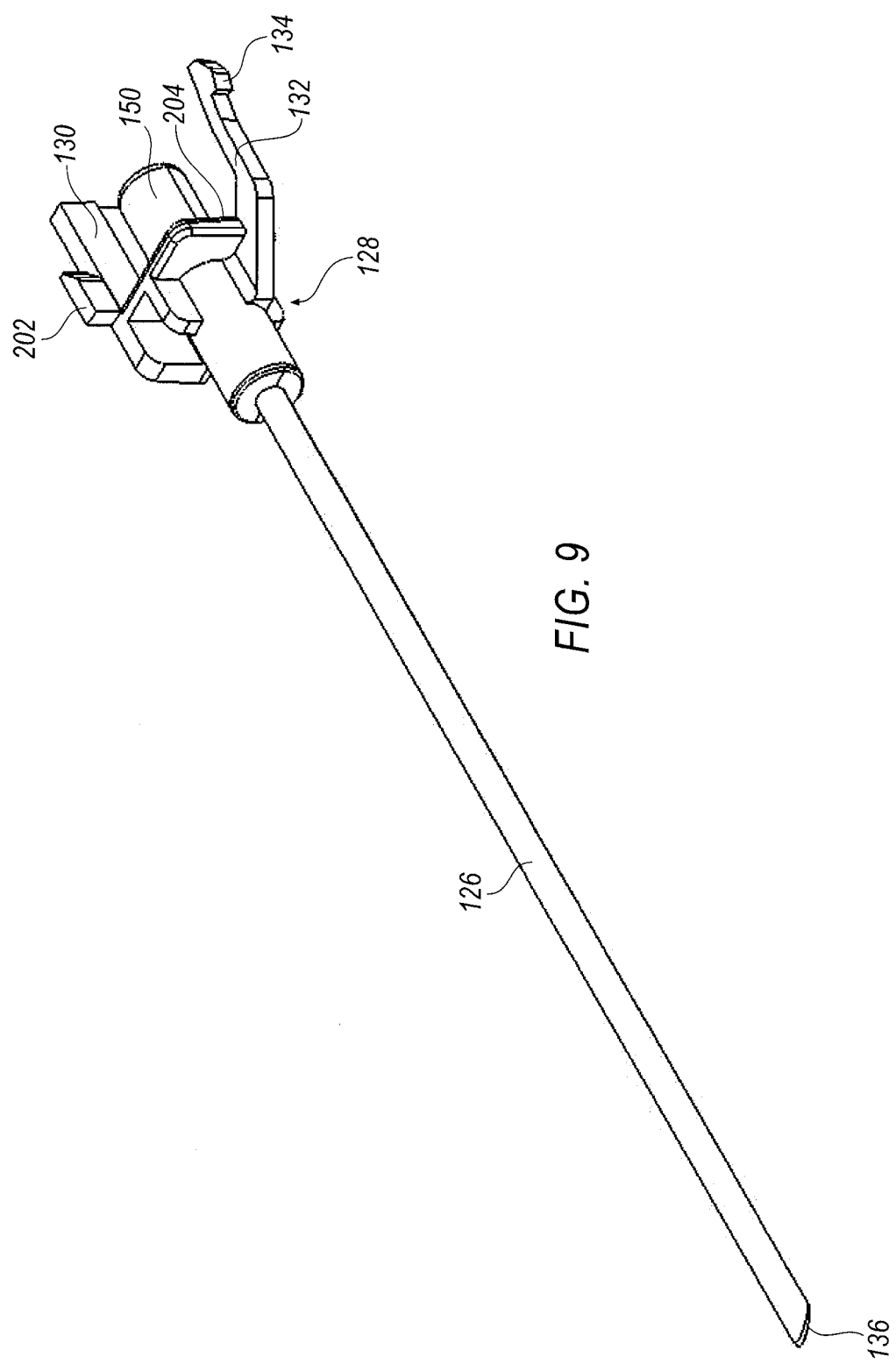
FIG. 9 is a perspective view of the cutting cannula assembly of FIG. 8.

Referring to FIG. 9, outer cannula assembly 74 includes an outer cutting cannula 126 that is fixedly attached to an outer cannula hub 128 at its proximal end. Outer cannula hub 128 includes a positioning member 130 on one side and a retaining member 132 on another. Retaining member 132 includes a retaining finger 134. A distal end 136 of outer cannula 126 is sharpened to sever tissue.

Referring to FIG. 2, outer cannula assembly 74 is assembled to stylet assembly 76 as follows. First, a bumper member 138 is positioned over stylet 16 and into contact with a mounting face 140. Support rib 82 is next slid onto stylet 16. Support rib 82 (best seen in FIG. 2) includes first and second mounting grooves 142, 144. First mounting groove 142 is configured to receive short leg member 124 of second arm sub-assembly 86 and leg member 112 of first arm sub-assembly 86. Second mounting groove 144 is configured to receive long leg member 122 of second arm sub-assembly 86. An outwardly extending spring mount 146 is formed on support rib 82. A biasing member 148, such as a spring is positioned on spring mount 146. Outer cannula hub 128 includes a spring mount 150 that receives an end of biasing member 148.

Referring now to FIGS. 3-6, pickup carriage 54 and cam member 52 will be described. Pickup carriage 54 includes a first elongated groove 152 and a second shortened groove 154. A mounting hole 156 is positioned opposite second groove 154. An access opening 158.

Cam member 52 includes a mounting member 160 that is received within mounting hole 156. A first pivot member 162 from cam member 52 is positioned within first groove 152 of pickup carriage 54. A second pivot member 164 from cam member 52 (seen in FIG. 2) is positioned within second groove 154. Retaining member 50 is positioned on an end of cam member 52 and is received within access opening 158.

A biasing member 166 received on a mounting portion 168 of pickup carriage 54. A distal end 170 of biasing member 166 contacts first pivot member 162 and biases first pivot member 162 toward a first end 172 of first groove 152. Pickup carriage 54 may further include a tang member 174 that partially retains a portion of biasing member 166.

Figure 3:
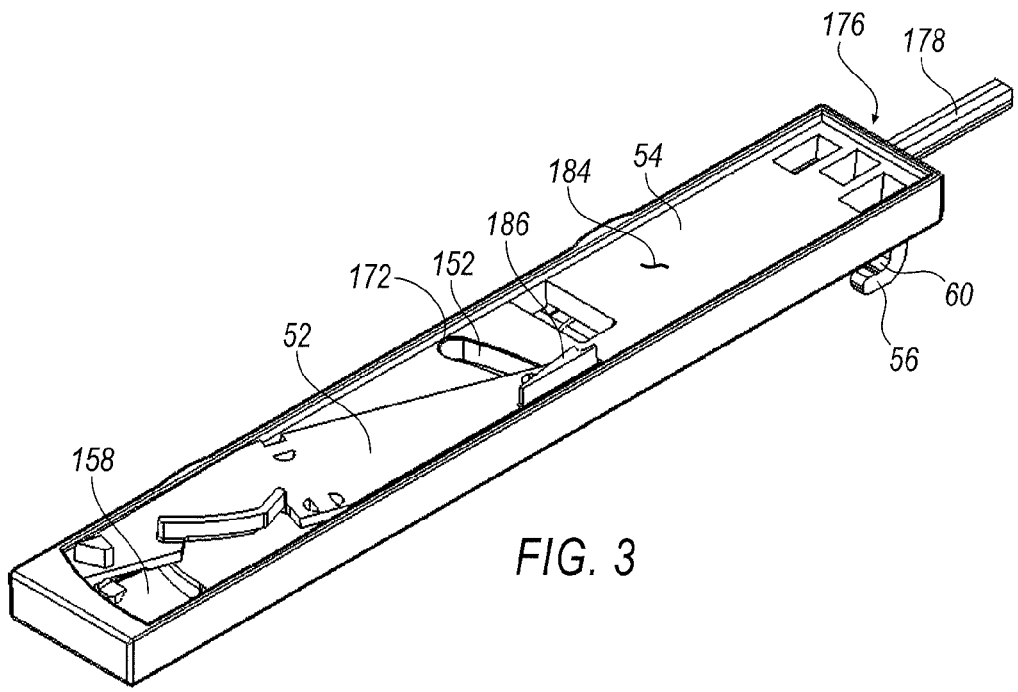
FIG. 3 is a perspective view of the underside of a pickup carriage assembly for use with the biopsy device.

A proximal end 176 of pickup carriage 54 includes a mounting post 178. A biasing member 180 is received on mounting post 178. An end of biasing member 180 engages an internal wall 182 formed by first and second housing members 14a and 14b when pickup carriage 54 is installed therewithin. When pickup carriage 54 is installed, holders 56 are oriented to extend upwardly through channel 58 formed through housing 14. Cam member 52 is installed on a bottom surface 184 of pickup carriage 54 as shown in FIG. 3.

Referring to FIGS. 12-20, operation of biopsy device 10 will now be described. Assuming biopsy device 10 is packaged in the fired position (see FIG. 12), biopsy device 10 must first be moved into the cocked position. To move biopsy device 10 into the cocked position, first release latch 18 is actuated to release actuation lever 40 from housing 14 (see FIG. 12). Actuation lever 40 is then depressed, pushing down on bridge member 30, which is attached to holders 56 of pickup carriage 54. Accordingly, when bridge member 30 is depressed, pickup carriage 54 is moved toward proximal end 44 of biopsy device 10.

As pickup carriage 54 moves toward proximal end 44 of biopsy device 10, a first pickup member 186 contacts a first tang member 188 that is carried on carrier member 120 that is part of second arm sub-assembly 88, and retracts vacuum chamber 108 proximally, as shown in FIG. 13. A first piston spring member 190 that is at least partially positioned over vacuum chamber 108, is compressed between a proximal face 192 of carrier member 120 and a first lower internal face 194 positioned within housing 14. A second spring member 196 is compressed between second end cap 104 and a second lower internal face 198 positioned within housing 14. This action also collapses the vacuum chamber 108, moving first end cap 102 towards chamber wall member 103. Air within vacuum chamber 108 is directed out through seal member 109 that is secured to proximal end 92 of stylet 16.

In one embodiment, seal member 109 is a configured as a duck-bill style valve member 109 (FIG. 2). Valve member 109 includes a body member 103 having an open distal end 105 that is connected to a tapered, duck bill, normally closed proximal end 107. Proximal end 107 includes a slit which is forced open when positive pressure is generated within stylet 16. Open distal end 105 is secured to proximal end 92 of stylet 16.

An alternative embodiment of seal member 109' is shown in FIGS. 21A-21D. Seal member 109' includes a body member 111 having an open distal end 119 and a normally closed proximal end. Adjacent to the proximal end of seal member 109' is a slit 113 that cooperates with a land member 115 to form a flap member 117. Slit 113 extends along a substantial portion of body member 111 such that land member 115 acts as a hinge for flap member 117. In operation, as positive pressure is generated within the system, flap member 117 will be forced open.

Spring member 180 biases pickup carriage 54 back toward a distal end of biopsy device 10. Actuation lever 40 is depressed again. The second depression of actuation lever 40 causes pickup carriage 54 to move in the proximal direction again. As pickup carriage 54 moves, a second pickup member 200 positioned on cam member 54 contacts a second tang member 202 that is carried on outer cannula hub 128. Such action retracts outer cannula assembly 74, moving toward distal end 136 thereof away from distal end 90 of stylet 16. Retaining member 132 is compressed inwardly until retaining finger 134 grips an internal ledge (not shown) formed in first housing member 14a. Retraction of outer cannula assembly 74 causes biasing member 148 to compress between a proximal face 204 of outer cannula hub 128 and a distal face 206 of support rib 82.

Spring member 180 biases pickup carriage 54 once again and actuation lever 40 is depressed a third time. The third depression of actuation lever 40 causes pickup carriage 54 to move proximally once again. As pick up carriage 54 moves proximally, first pickup member 186 engages with fitting member 116 that is carried on carrier member 114 of first arm sub-assembly 86 and pulls first arm sub-assembly 86 towards second arm sub-assembly 88. Once carrier 114 of first arm sub-assembly 86 reaches carrier 120 of second arm sub-assembly 88, stylet 16 is pulled into outer cannula 126 and stylet 16 is locked into the cocked position. On the third depression, actuation lever 40 locks down and latch release assembly 48 retains lever 40 against housing 14 (see FIG. 15), thereby providing a tactile indicator that biopsy device is in the cocked position.

Biopsy device may also include a visual indicator to indicate that biopsy device 10 is in the cocked position. In one embodiment, at least leg member 112 of first arm sub-assembly 86 may be constructed of a particular color that is different than the color of housing 14 and that will be visible through a window 208 only when biopsy device 10 is in the cocked position. For example, leg member 112 may be formed from a green material such that a portion of the green material is visible through window 208 when biopsy device 10 is in the cocked position so as to be in the "biopsy ready position." In contrast, when stylet 16 is in a non biopsy ready position, leg member 112 will be positioned away from indicator window 208.

Once in the cocked position, or biopsy ready position, a biopsy may be performed. The operation will now be explained.

Typically, before a biopsy is performed, a targeted area must be identified. Any suitable method may be used to identify a targeted area for biopsy. Such methods include, but are not limited to, the methods and use of the devices described in co-pending application Ser. No. 10/649,068, the contents of which are incorporated herein by reference in its entirety.

Next, the entry site is prepared, as required (such as applying anesthesia, cleaning the biopsy area, etc.). During this step, an introducer assembly 12 (see FIG. 1) may be positioned over outer cannula 112 to provide a pathway to the target area. Introducer assembly 12 will be explained in further detail below.

Next, a tip of stylet 16 is placed at the targeted area. In one embodiment, stylet 16 may be fired prior to inserting biopsy device 10 into the patient. In another embodiment, stylet 16 is not fired until after biopsy device 10 is inserted into the patient. In one embodiment, the position and orientation of biopsy device 10 is maintained during the firing process.

Figure 16:
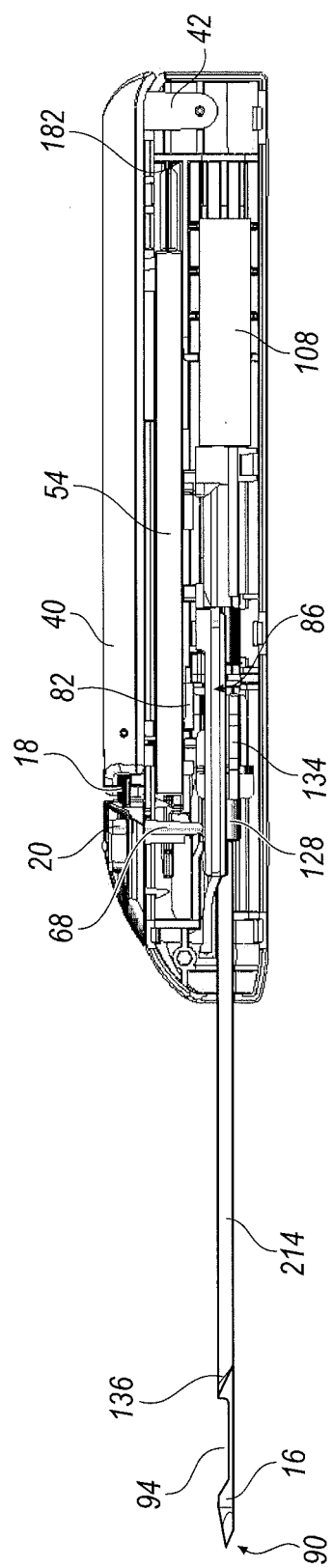
FIG. 16 is a side elevational view of the biopsy device after the stylet has been fired away from a housing of the biopsy device.
Figure 21A:
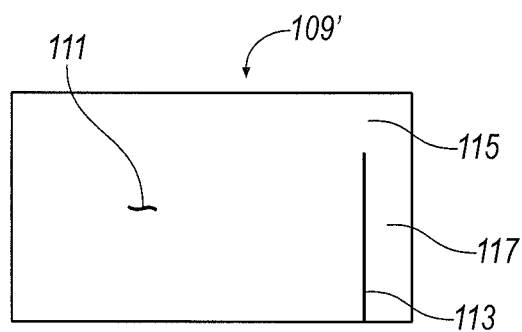
FIG. 21A-21D are various views of a valve member.
Figure 21C:
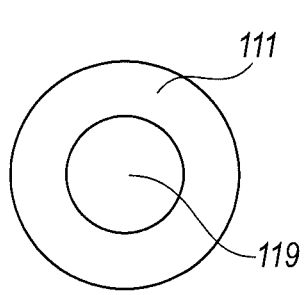
Figure 21B:
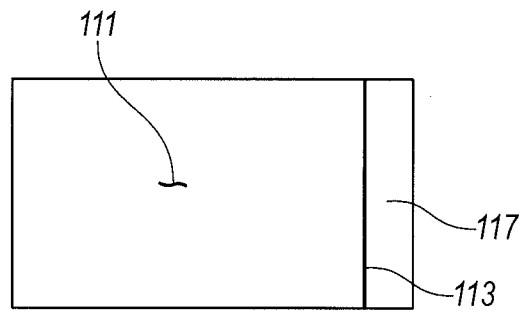
Figure 21D:
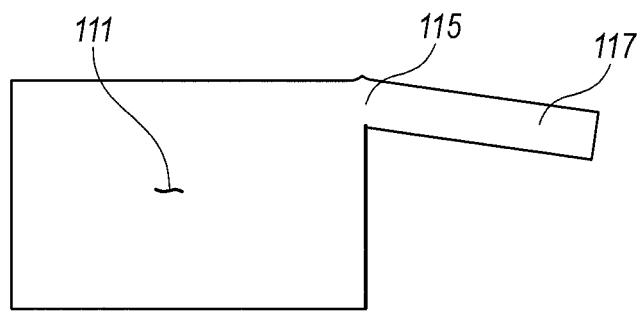

A stylet release or firing member 20 is depressed, thereby releasing stylet assembly 76 from its cocked position into the fired position (FIG. 16). Such action exposes tissue opening 94 into which tissue may prolapse. Tissue receiving opening 94 is connected to inner lumen 96. Inner lumen 96 is connected to vacuum chamber 108.

To differentiate between stylet release member 20 and an outer cannula release member 22, stylet release member 20 may be a different color than housing 14 or outer cannula release member 22 (to be described below) to allow a user to visually differentiate between the two release members. In one embodiment, one of stylet and outer cannula release members 20, 22 may alternatively include a tactile indicator, such as a raised bump 210 on the release member, to allow a user to feel the differences between the two release members (see, e.g., FIGS. 1 and 11).

After stylet release member 20 is actuated, outer cannula release member 22 is then actuated. This action will release outer cannula assembly 78. Outer cannula assembly 78 is forced over stylet 16 by biasing members/springs 148, 190, and 196, such that outer cannula assembly 78 rapidly fires forward. As outer cannula assembly 78 is fired forward, vacuum chamber 108 is expanded so as to create a vacuum by drawing air through tissue opening 94 and lumen 96, and entering into vacuum chamber 108 through notch 110. A further explanation of the vacuum chamber may be found in commonly owned and co-pending U.S. application Ser. No. 11/389,274, the contents of which are incorporated herein by reference in its entirety.

In one embodiment (not shown), a vacuum valve having a slit that creates a flap may be provided that selectively covers the notch. When stylet 16 is fired forward, positive pressure generated inside vacuum chamber 108 closes the valve flap to prevent pressure from reaching the inside of lumen 96. When outer cannula 74 fires forward, the negative pressure inside vacuum chamber 108 opens the valve, allowing vacuum to be delivered to tissue opening 94 in stylet 16, through lumen 96.

As outer cannula assembly 78 is fired and vacuum is generated by the expansion of vacuum chamber 108, the vacuum biases tissue toward tissue opening 94 and holds tissue in place while outer cannula 74 slides over tissue opening 94. As outer cannula 74 slides, sharpened distal end 136 slices through the tissue, thereby severing the tissue so as to leave a biopsy core 212 within tissue opening 94.

Once biopsy core 212 is acquired, to retrieve biopsy core 212 from biopsy device 10, biopsy device 10 is removed from the patient. If an introducer assembly 12 is used, it is kept in position within the patient. Once removed from the patient, release member 18 is depressed once again to release latch member 26. Latch member 26 is depressed twice to pull back outer cannula 74 so as to expose tissue opening 94 (see FIGS. 18-20) and biopsy core 212. To obtain additional biopsy cores 212, the latch member 26 is depressed a third time (FIG. 20) to retract stylet 16 into the biopsy ready position.

Figure 11:
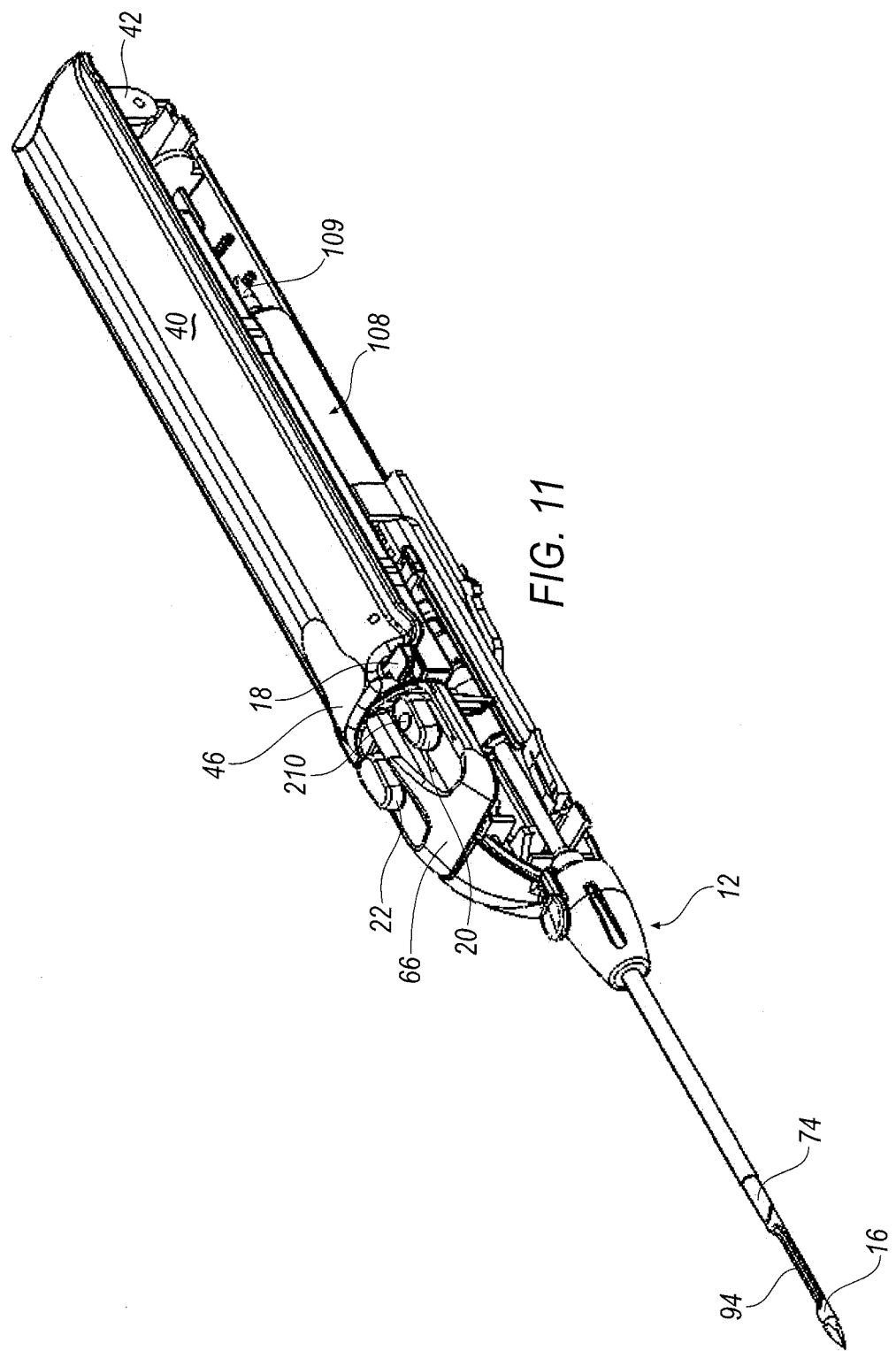
FIG. 11 is a partial cut-away perspective view of the biopsy device with the introducer assembly attached to the front portion thereof.

Referring to FIGS. 1 and 11, introducer assembly 12 will now be explained. Introducer assembly 12 includes an introducer cannula 214 that is fixedly connected to an introducer hub 216. Introducer cannula 214 is hollow and is sized to slide over outer cannula 74 so as to be spaced proximally from distal end of outer cannula 74. Introducer hub 216 may include a normally closed valve (not shown) and includes an opening that is in communication with introducer cannula 214. Disposed on introducer hub 216 is a selectively releasable latch member 218 that includes a connecting member 220 and a releasing member 222. Releasing member 222 is received within an opening 224 to secure introducer assembly 12 to biopsy device 10.

In operation, introducer assembly 12 is positioned over outer cannula 74 and slid along outer cannula 74 until connecting member 220 of latch member 218 is received within opening 224, thereby connecting introducer assembly 12 to biopsy device 10. Introducer assembly 12 may be connected to biopsy device 10 either before or after biopsy device is placed in the biopsy ready position. Once connected, biopsy device 10 is inserted into the patient with introducer cannula 214. Introducer cannula 214 operates to maintain a pathway to the biopsy site.

Once biopsy cores 212 are taken, biopsy device 10 may be detached from introducer assembly 12 by depressing releasing member 222 such that connecting member 220 is released from opening 224. Once freed, introducer cannula 214 remains within the patient's body, to maintain the pathway to the biopsy site. Use of introducer assembly 12 minimizes trauma to the patient and eliminates the need for multiple reinsertions of biopsy device 10, as well as permits access to the biopsy site for treatment and other post biopsy activities. As such, after the biopsy cores 212 are removed from tissue opening 94, biopsy device 10 may be reinserted into introducer cannula 214 to take addition biopsy cores 212.

Alternatively, if desired, a biopsy marker (not shown) may be deployed into the biopsy cavity after biopsy cores 212 have been taken. In such a case, a site marker deployment device may be inserted within introducer assembly 12 after biopsy device 10 is removed therefrom. Once such example of a site marker deployment device is disclosed in commonly owned and co-pending application Ser. No. 11/238,295, the contents of which are incorporated herein by reference in its entirety.

Figure 22:
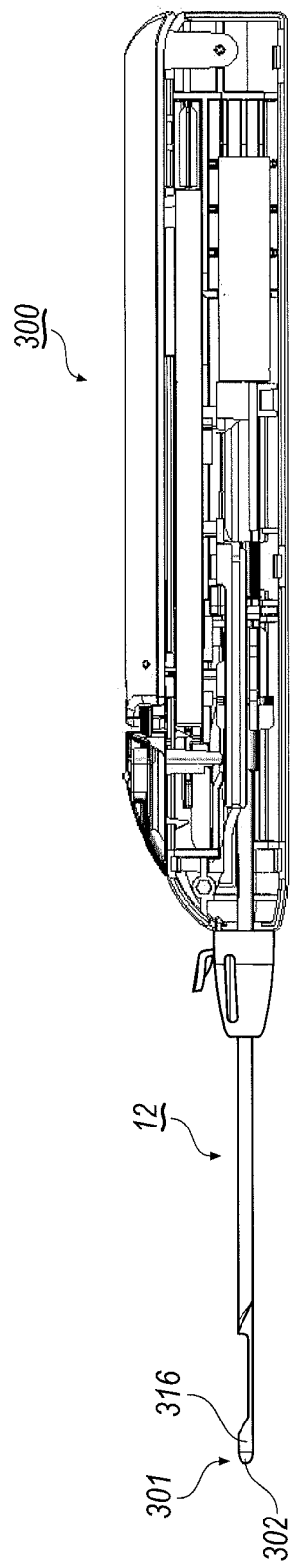
FIG. 22 is a partial cut-away side elevational view of an alternative embodiment of a biopsy device, after the actuating lever has been depressed a second time, thereby retracting the cutting cannula.
Figure 23:
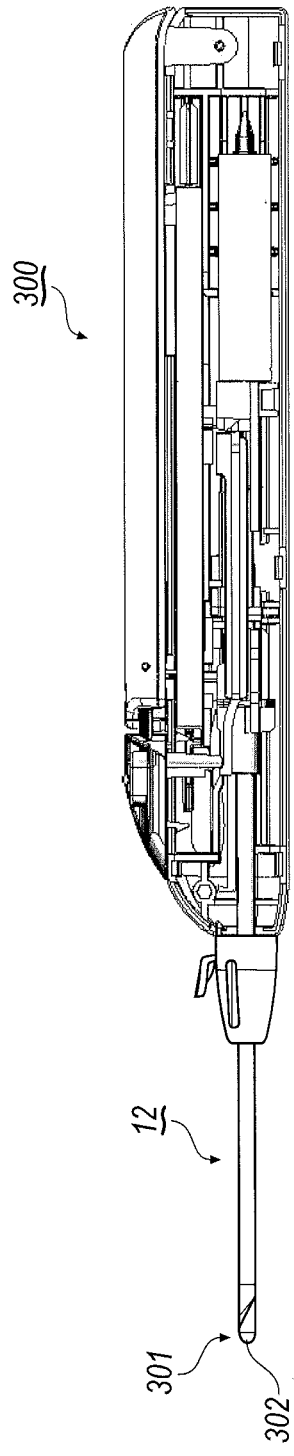
FIG. 23 is a side elevational view of the biopsy device in FIG. 22, after the actuating lever has been depressed a third time, thereby retracting the distal end inner cannula, within the cutting cannula.

Referring now to FIGS. 22 and 23, another embodiment of a biopsy device 300 is illustrated. Biopsy device 300 includes the same components as biopsy device 10, except that distal end 301 of stylet 316 is formed with a blunt tip 302 rather than a trocar tip, as shown with stylet 16.

Blunt tip 302 is useful for those instances where a lesion to be biopsied is close to the chest wall. More specifically, the length of blunt tip 302 is shorter than the length required for a trocar tip, thereby permitting access to a lesion close to a chest wall.

However, because there is no trocar tip, to position biopsy device 300 at a target area within the body, a separate trocar device (not shown) must be used to create a pathway for the stylet 316 and cutting cannula 74. An example of a trocar device is shown and described in commonly owned U.S. Pat. No. 7,347,829, the contents of which are incorporated in its entirety. As may be seen, the trocar device is defined by an elongated body having a sharp distal end. The proximal end of the trocar device may also include handle.

In operation, once the target area is defined, the trocar device is inserted into the patient to create a pathway to the target site. In one arrangement, introducer assembly 12 is used with the trocar device. More specifically, and as described in U.S. Pat. No. 7,347,829, trocar device is inserted into the introducer cannula 214 prior to insertion of the trocar device into the patient's body. A target confirmation device (as described and disclosed in U.S. Pat. No. 7,347,829) may then be used to verify that the pathway created by the trocar device has reached the target site. In one embodiment, the trocar device may be used as the target confirmation device. In another embodiment, the target confirmation device is a separate component that may inserted into the pathway after removal of the trocar device. When the trocar device is removed from the patient's body, the introducer cannula 214 will remain within the patient's body to hold open the pathway to the target area.

Once the pathway to the target site is defined, the distal end 301 of the biopsy device 300 is inserted into the introducer cannula 214 until distal end 301 extends outwardly from a distal end of the introducer cannula 214. Releasing member 222 may be inserted into the opening 224 formed on the housing of biopsy device 300 in a similar fashion as described in connection with the biopsy device 10. Once inserted through the introducer cannula 214, the biopsy device 300 may be operated in the same manner as described in connection with biopsy device 300.

While the embodiments of the present invention has been particularly shown and described with reference to the foregoing preferred embodiments, it should be understood by those skilled in the art that various alternatives to the embodiments of the invention described herein may be employed in practicing the invention without departing from the spirit and scope of the invention as defined in the following claims. It is intended that the following claims define the scope of the invention embodiments within the scope of these claims and their equivalents be covered thereby. This description of the invention should be understood to include all novel and non-obvious combinations of elements described herein, and claims may be presented in this or a later application to any novel and non-obvious combination of these elements. The foregoing embodiment is illustrative, and no single feature or element is essential to all possible combinations that may be claimed in this or a later application.

What is claimed is:

1. A biopsy device, comprising:
a stylet having a lumen with an open proximal end and a tissue receiving opening near a distal end thereof;
an outer cannula slidably disposed over the stylet, the outer cannula having an open distal end with a cutting edge formed thereon; and
a vacuum chamber in fluid communication with the lumen of the stylet,
wherein the outer cannula is configured to be actuated so as to causes a vacuum to be delivered to the tissue receiving opening through the lumen of the stylet before the outer cannula advances distally over the tissue receiving opening, and
wherein the outer cannula is mechanically connected to the vacuum chamber such that advancement of the outer cannula over the stylet causes movement of a wall of the vacuum chamber, thereby expanding the vacuum chamber.

2. The biopsy device of claim 1, wherein stylet is configured to be advanced distally before the outer cannula is advanced distally.

3. The biopsy device of claim 1, further comprising an actuation lever that is configured to selectively position the stylet and the outer cannula into a cocked position, wherein the actuation lever is configured to be actuated in a multi-step sequence to place the stylet and outer cannula in the cocked position, wherein a first actuation of the actuation lever is configured to collapse the vacuum chamber, wherein a second actuation of the actuation lever is configured a second time to retract the outer cannula, and wherein a third actuation of the actuation lever is configured to retract the stylet.

4. The biopsy device of claim 1, wherein actuating the outer cannula partially expands the vacuum chamber that is fluidly connected to the lumen of the stylet.

5. The biopsy device of claim 4, wherein the vacuum chamber comprises first and second seal members and a cylinder, wherein the first seal member is moveably mounted with respect to the second seal member, and wherein the second seal member is fixedly connected to the stylet.

6. The biopsy device of claim 5, further comprising a one-way valve member attached to the proximal end of inner cannula.

7. The biopsy device of claim 1, wherein the stylet extends through the vacuum chamber and further comprising a vacuum opening formed through the sidewall of the stylet and in communication with the lumen, wherein the vacuum opening is positioned within the vacuum chamber.

8. The biopsy device of claim 7, further comprising a vacuum valve that is positioned over the vacuum opening, wherein the vacuum valve is configured to selectively open when the vacuum chamber is expanded so as to deliver vacuum to the lumen.

9. A biopsy device, comprising:
a stylet and an outer cannula movably mounted to a handpiece,
the stylet having a lumen with an open proximal end and a tissue receiving opening disposed adjacent a distal end thereof and in communication with the lumen;
an outer cannula slidably mounted over the stylet, the outer cannula having an open distal end with a cutting edge formed thereon; and
a vacuum chamber in fluid communication with the lumen of the stylet,
wherein the stylet is configured to be advanced distally with respect to the handpiece and the outer cannula to expose the tissue receiving opening,
the outer cannula is configured to be actuated so as to cause a vacuum to be delivered to the tissue receiving opening through the lumen of the stylet before the outer cannula advances distally over the tissue receiving opening, and
the outer cannula is mechanically connected to the vacuum chamber such that advancement of the outer cannula over the stylet causes movement of a wall of the vacuum chamber, thereby expanding the vacuum chamber.

* * * * *